US005669871A

United States Patent [19]

Sakiyama

[11] Patent Number: 5,669,871

[45] Date of Patent: Sep. 23, 1997

[54] ENDOSCOPE MEASUREMENT APPARATUS FOR CALCULATING APPROXIMATE EXPRESSION OF LINE PROJECTED ONTO OBJECT TO MEASURE DEPTH OF RECESS OR THE LIKE

[75] Inventor: Katsunori Sakiyama, Itsukaichi-machi, Japan

[73] Assignee: Olympus Optical Co., Ltd., Tokyo, Japan

[21] Appl. No.: 371,979

[22] Filed: Jan. 12, 1995

[30] Foreign Application Priority Data

Feb. 21, 1994 [JP] Japan .................................... 6-022579

[51] Int. Cl.$^6$ ........................................ A61B 1/00

[52] U.S. Cl. .......................... 600/117; 348/135; 348/136; 348/141; 128/653.1

[58] Field of Search ................................. 348/65, 67, 68, 348/45, 141, 72, 74, 135, 136, 137, 140; 356/2, 241, 376; 600/103, 108, 117, 160, 170, 118; 364/413.13

[56] References Cited

U.S. PATENT DOCUMENTS

| | | | |
|---|---|---|---|
| 4,141,038 | 2/1979 | Gecewicz et al. | 348/141 |
| 4,361,830 | 11/1982 | Homa et al. | 382/199 |
| 4,396,944 | 8/1983 | McKenney et al. | 348/141 |
| 4,767,212 | 8/1988 | Kitahashi et al. | 356/379 |
| 4,834,070 | 5/1989 | Saitou | 600/108 |
| 4,935,810 | 6/1990 | Nonami et al. | 348/45 |
| 4,958,932 | 9/1990 | Kegelman et al. | 356/383 |
| 4,980,763 | 12/1990 | Lia | 348/67 |
| 5,054,491 | 10/1991 | Saito et al. | 128/662.06 |
| 5,061,995 | 10/1991 | Lia et al. | 348/68 |
| 5,070,401 | 12/1991 | Salvati et al. | 348/141 |
| 5,090,400 | 2/1992 | Saito | 600/108 |
| 5,104,227 | 4/1992 | Uesugi et al. | 356/376 |
| 5,150,254 | 9/1992 | Saitou | 600/108 X |
| 5,153,721 | 10/1992 | Eino et al. | 382/152 |
| 5,202,758 | 4/1993 | Tamburrino | 600/109 X |
| 5,434,669 | 7/1995 | Tabata et al. | 356/345 |

*Primary Examiner*—Richard J. Apley
*Assistant Examiner*—David R. Risley
*Attorney, Agent, or Firm*—Armstrong, Westerman, Hattori, McLeland & Naughton

[57] ABSTRACT

A line projection part provided on a distal-end part of an endoscope for projecting a light of a line toward the side of an object. A plurality of points are assigned on a line which is projected so as to pass through a recess or the like which resides in an object surface, to calculate an approximate line which expresses the line three-dimensionally. Further, a measurement point is assigned onto the line which passes through the recess, to find a three-dimensional coordinate thereof. A distance from the three-dimensional coordinate to the approximate line is found to calculate a depth of the recess or the like.

29 Claims, 24 Drawing Sheets

FIG.13
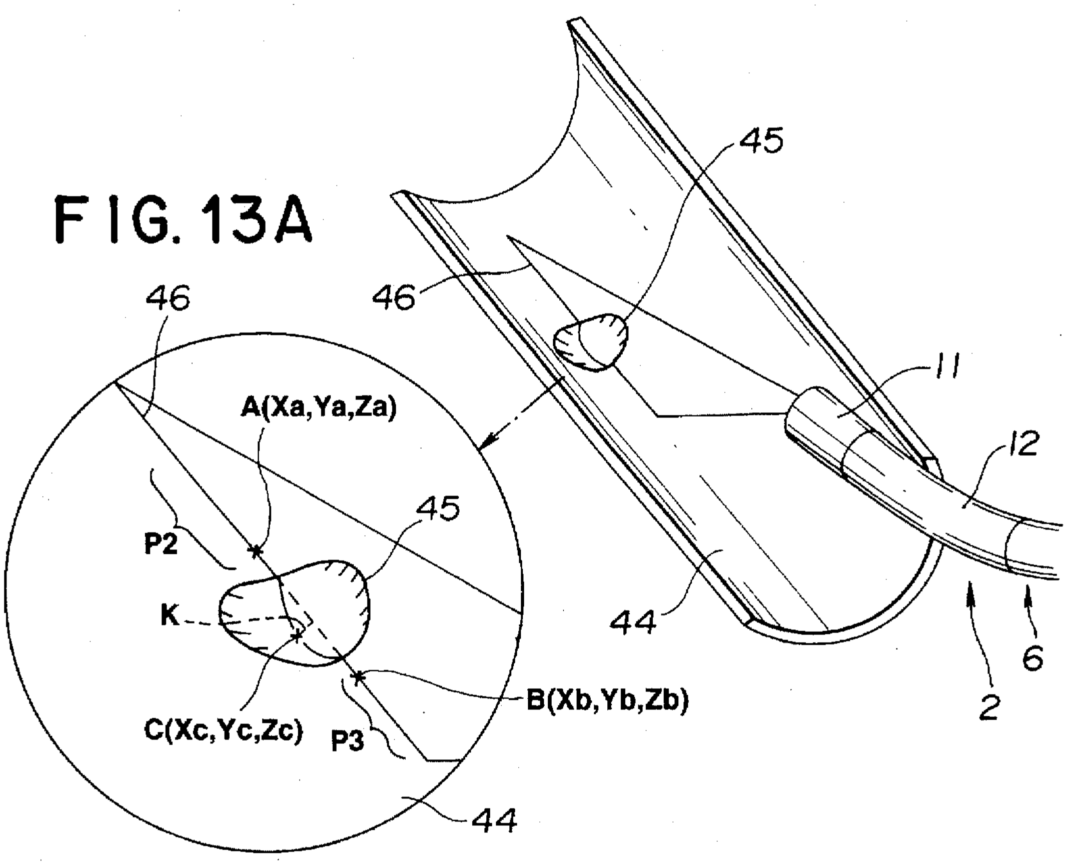
FIG. 13A
FIG.14
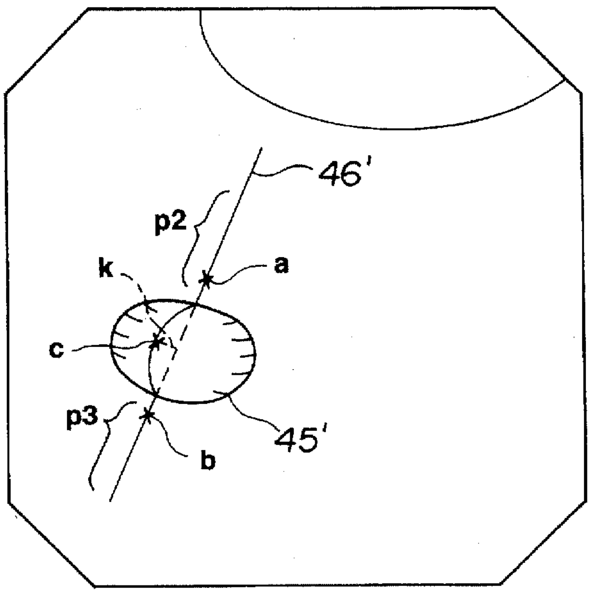

| ACTUAL OBJECT DISTANCE | OBJECT DISTANCE DUE TO ORIGIN op | CORRECTED ORIGIN COORDINATE |
|---|---|---|
| 5 | 4 | 33 |
| 10 | 9 | 8 |
| 15 | 13 | 5 |
| 20 | 18 | 4 |
| 25 | 22 | 4 |
| 30 | 26 | 3 |
| 35 | 29 | 3 |
| 40 | 35 | 3 |

ENDOSCOPE MEASUREMENT APPARATUS FOR CALCULATING APPROXIMATE EXPRESSION OF LINE PROJECTED ONTO OBJECT TO MEASURE DEPTH OF RECESS OR THE LIKE

BACKGROUND OF THE INVENTION

1. Field of the Invention

The present invention relates to an endoscope measurement apparatus which is provided with length-measurement function in which a line is projected onto an object, an approximate expression with respect to a criterion or standard line portion is found in the line, and a distance from a three-dimensional position of a recess or a projection to the approximate expression is found, in order to measure a depth of the recess or a height of the projection.

2. Description of the Related Art

In recent years, an endoscope has been widely utilized in which an elongated insertion part is inserted into a body cavity to thereby observe internal organs or the like within the body cavity, or a treatment took which is inserted into a treatment-tool channel is used, as occasion demands, so that the endoscope can conduct various kinds of therapy treatments or dispositions.

Further, also in a field of industry, an industrial endoscope has widely been used for observation and inspection of flaws or cracks, etching or corrosion or the like within boilers, turbines, engines, chemical plants or the like.

U.S. Pat. No. 4,980,763 discloses measurement means for object configuration or shape due to an optical cutting method or a light-section method in which a contrast light in the form of a line is radiated or emitted from an illumination light source at a distal part of an endoscope.

Japanese Patent Unexamined Publication No. SHO 51-95866 (95866/1976) discloses means which uses an optical cutting method to observe a direction of irregularity in an inner surface of a pipe.

Japanese Patent Publication No. HEI 2-43487 (43487/1990) discloses means for projecting a light ray beam from an endoscope distal end to an object surface to measure a distance to an object.

The optical cutting method disclosed in U.S. Pat. No. 4,980,763 is capable of conducting the measurement of a length on the line, the measurement of the object shape in which is varied smoothly without the line being broken or being interrupted, and the measurement of a step in which correspondence of the broken line is clear or definite.

However, U.S. Pat. No. 4,980,763 discloses only the measurement method in the case where an object surface is perpendicular to an axis of the endoscope, but does not disclose a method of measuring the depth in the case where the pipe inner surface or the like, for example, is observed obliquely by the endoscope, or the like. Generally, however, in the case where the pipe inner surface is observed by the measurement endoscope, a relative angle between the pipe inner surface and the endoscope distal end is unknown and, accordingly, it is impossible by the prior art method to assure measurement accuracy.

Japanese Patent Laid-Open Publication No. SHO 51-95866 shows the means which uses the optical cutting method to observe a direction of the irregularity on the pipe inner surface. In this technique, however, the pipe inner surface must be observed at a perpendicular angle. Moreover, a method of depth measurement is not totally disclosed.

Japanese Patent Publication No. HEI 2-43487 discloses the means in which the light ray beam is projected from the endoscope distal end to the object surface to measure the distance to the object. However, Japanese Patent Publication No. HEI 2-43487 does not totally disclose a method of depth measurement in the object surface.

SUMMARY OF THE INVENTION

An object of the present invention is to provide an endoscope measurement apparatus capable of accurately measuring a depth of a pipe inner surface, or the like, even by observation in an oblique direction, in an optical cutting method which uses an endoscope.

Another object of the invention is to provide an endoscope measurement apparatus which can easily conduct measurement of a recess or a projection.

According to the invention, there is provided an endoscope measurement apparatus comprising:

an endoscope including an elongated insertion part, an illumination optical system provided on the side of a distal end of said insertion part, for outputting an illumination light to an object, an object optical system (provided on the side of the distal end of said insertion part) for imaging the object which is illuminated by said illumination light, reference-line projection means (provided on the side of the distal end of said insertion part) for projecting a reference line which passes through a recess or a projection residing on a plane of said object, and an image-pickup element for photoelectrically converting or transferring an image on the basis of said object optical system;

signal processing means for conducting signal processing with respect to said image-pickup element, to generated an image signal;

display means for displaying an image which corresponds to said object upon which said reference line is superimposed, by the fact that said image signal is inputted;

position assignment means for assigning an optional position of said image; and operation means for conducting calculation of an operation of an expression of an approximate line which expresses a standard line three-dimensionally, regarding the reference line passing through said plane as the standard line of the measurement, calculation of a three-dimensional coordinate position corresponding to a point which is assigned by said position assignment means, on the reference line, and calculation of a distance between said approximate line and said three-dimensional coordinate position to calculate a depth of said recess or a height of a projection.

Thus, the endoscope measurement apparatus can find the distance from the point which is assigned on the reference line which passes through said recess or said projection with respect to the approximate line which serves as the standard reference line with respect to the standard line which passes through said plane.

BRIEF DESCRIPTION OF THE DRAWINGS

FIG. 1 to FIG. 15D relate to a first embodiment of the invention, FIG. 1 being an outer appearance view showing a whole arrangement of an endoscope apparatus according to the first embodiment;

FIG. 2 is a whole arrangement view showing the endoscope apparatus;

FIG. 3 is a cross-sectional view showing structure or construction of an endoscope distal-end part;

FIG. 6 is a block diagram showing a schematic arrangement of an electric system of the endoscope apparatus;

FIG. 7 is a view in which a laser line is projected onto an object surface which is in parallel with a distal-end surface;

FIG. 8 is an explanatory view of the relationship between a measurement point and an optical system at a B—B cross-sectional position in FIG. 7;

FIG. 9 is an explanatory view showing a state or an aspect in which the laser line is projected on the object surface which is oblique to the distal-end surface;

FIG. 10 is a side elevational view of FIG. 9;

FIG. 11 is an explanatory view showing an image-pickup image in FIG. 9;

FIG. 13A is an explanatory view showing an aspect in which the laser line is projected on a pipe inner surface which has a recess;

FIG. 13B is a magnified view of the recess shown in FIG. 13A;

FIG. 14 is an explanatory view showing an image which is image-picked up, corresponding to FIG. 13;

FIG. 15B to FIG. 15D are flow charts showing the processing order of a modification of FIG. 15A;

FIG. 32 to FIG. 37 relate to a fifth embodiment of the invention, FIG. 32 being a whole arrangement view showing an endoscope measurement apparatus according to the fifth embodiment;

FIG. 33 is a cross-sectional view showing construction on the side of a distal end of an endoscope;

FIG. 34 is a front elevational view of a glass plate as viewed from a front elevational direction of FIG. 33;

FIG. 36 is an explanatory view showing an image which is image-picked up, corresponding to FIG. 35A; and FIG. 37 is a view showing a projected planar surface which passes through the recess which is cross-sectioned by a projecting line of the shadow.

DESCRIPTION OF THE PREFERRED EMBODIMENTS

Various embodiments of the invention will hereunder be described in detail with reference to the accompanying drawings.

Figure 1:
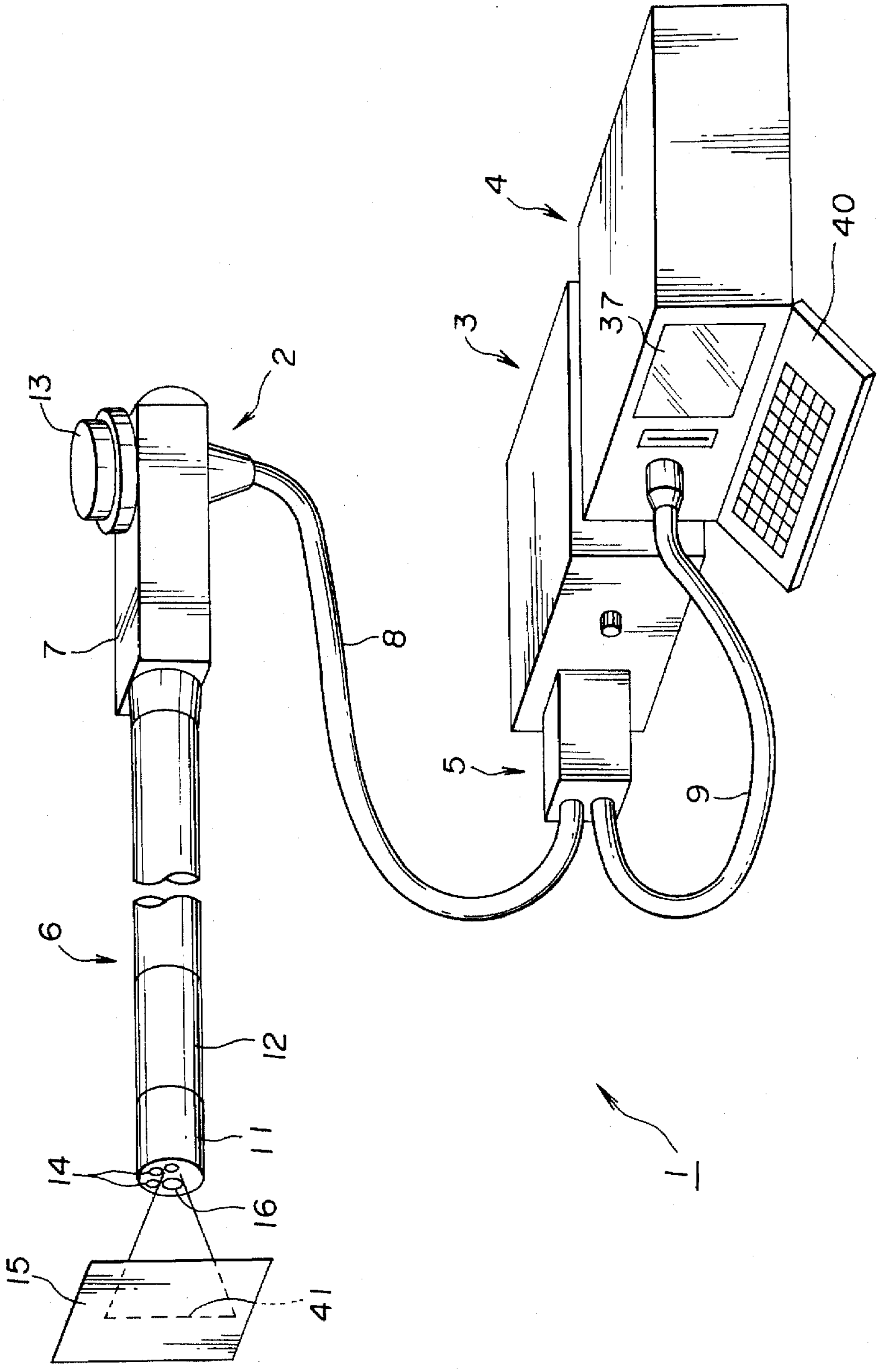
Figure 2:
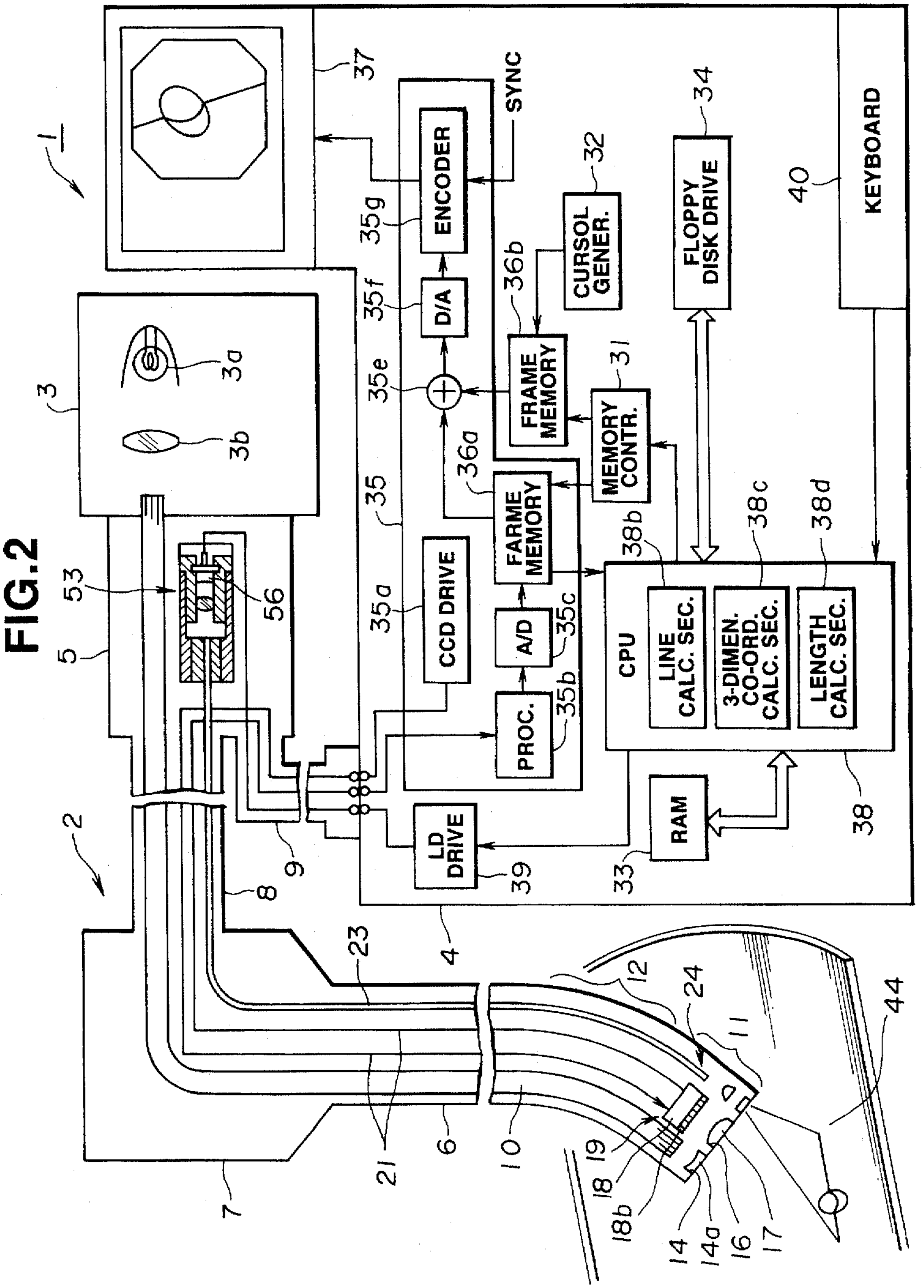

As shown in FIG. 1 and FIG. 2, an endoscope measurement apparatus 1 according to a first embodiment comprises an electronic endoscope 2 having built-in image pickup means, an illumination light source 3 to which the electronic endoscope 2 is connected, for supplying an illumination light to the electronic endoscope 2, a measurement unit 4 for conducting signal processing with respect to the image pickup means of the electronic endoscope 2, the measurement unity having fee function of conducting length measurement, and a laser light source 5 provided at a connection between the electronic endoscope 2 and the illumination light source 3, for generating a laser light.

The electronic endoscope 2 comprises an elongated insertion part 6 having elasticity, an operating part 7 which is provided at a rear end of the insertion part 6 and which is gripped, and a universal cord 8 extending from the operating part 7. The universal cord 8 has a distal end thereof which is connected to the laser light source 5. Further, an electrical cable 9 extends from the laser light source 5 and is connected to the measurement unit 4 which contains therein a signal processing system for measuring length.

The insertion part 6 has a rigid distal-end part 11, and a bendable curvature part 12 adjacent to the distal end part 11.

A curvature operating knob 13 which is provided on the operating part 7 is moved angularly to thereby be able to curve the curvature part 12.

A light guide 10 for transmitting the illumination light is inserted into the insertion part 6 and into the universal cable 8 to transmit the illumination light which is supplied from a lamp 3*a* within the illumination light source 3, to an end face through a lens 3*b*. The transmitted illumination light is outputted forwardly through an illumination lens 14*a* which is respectively mounted on two illumination windows 14, 14 (only one is shown in FIG. 2) of the distal-end part 11, to illuminate a forward object surface 15.

Figure 3:
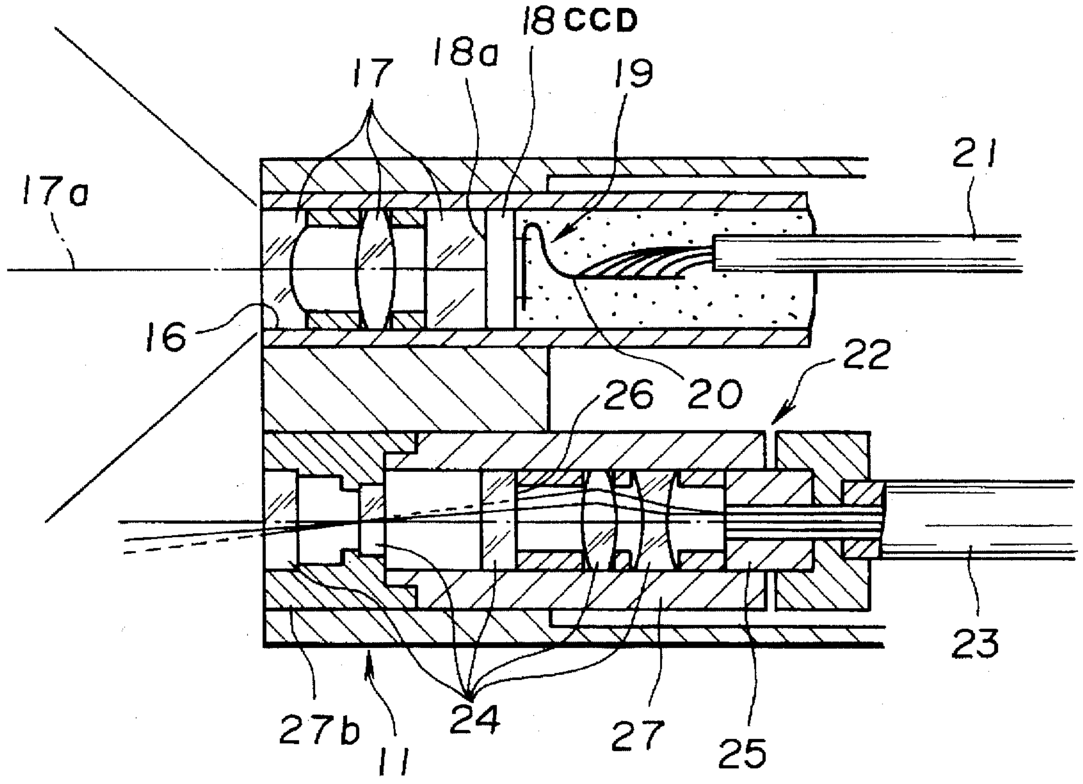

An observation window 16 is provided adjacent to the illumination windows 14, 14. As shown in FIG. 3, an object lens system 17 is mounted on the observation window 16. A charge-couple device (abridged as "CCD") 18, for example, is arranged as a solid-state image pickup element on a focal plane of the object lens system 17, for focusing an optical image of the object surface 15 which serves as the illuminated object, onto the CCD 18. A mosaic filter 18*b*, for example, is mounted on a photoelectric conversion surface of the CCD 18, to conduct optical color separation for every pixel.

The object lens system 17 and the CCD 18 cooperate with each other to form an image pickup part (or an image pickup system) 19 which acquires an image-picked-up image. The electronic endoscope 2 is an endoscope of a different vision type whose observation field-of-view is a direction which is in parallel to an axis of the insertion part.

A lead which projects from a rear surface of the CCD 18 which converts the optical image image-formed by the object lens system 17, to an electrical signal is connected to a flexible substrate 20. The flexible substrate 20 is bent, and a distal end of a signal cable 21 is connected to the side of a rear end which extends rearwardly. The signal cable 21 is inserted into the universal cord 8 from the operation part 7, and further passes through the electrical cable 9 so that the rear end thereof is connected to the measurement unit 4.

Figure 7:
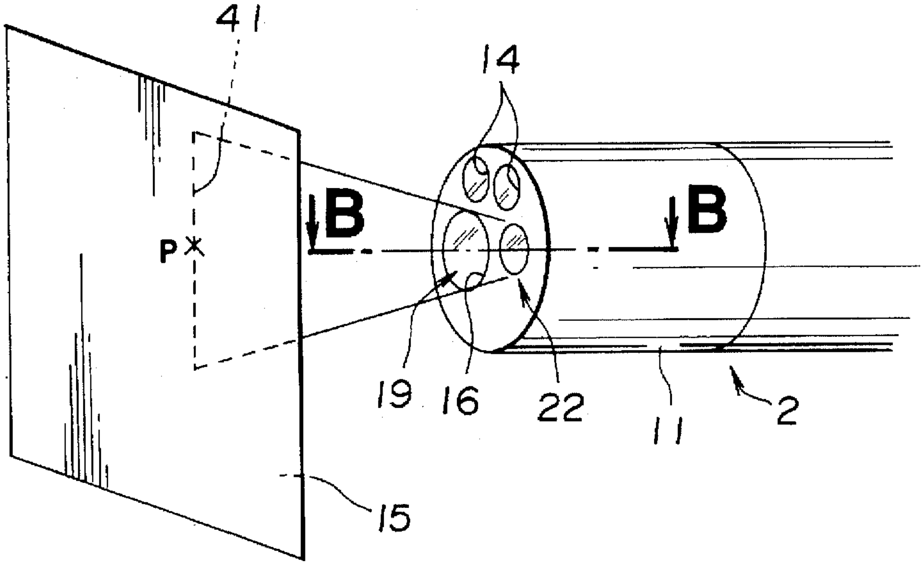

Moreover, as shown in FIG. 3, a laser-line projection part 22 is mounted on a window which is formed adjacent to the observation window 16. The laser light which is generated by a laser diode 56 within the laser light source 5 is transmitted by an optical fiber 23. The transmitted laser light passes through a laser-line projection lens system 24, and the laser light in the form of a line is projected onto the side of the object surface 15 refer to FIG. 1 or FIG. 7, FIG. 2 shows an aspect projected onto a pipe inner surface 44), to form a laser line 41 on the object surface 15. The arrangement is such that the laser line 41 which is formed by projection onto the object surface 15 can be used to measure the depth or the like (measurement due to the optical cutting method).

Figure 4A:
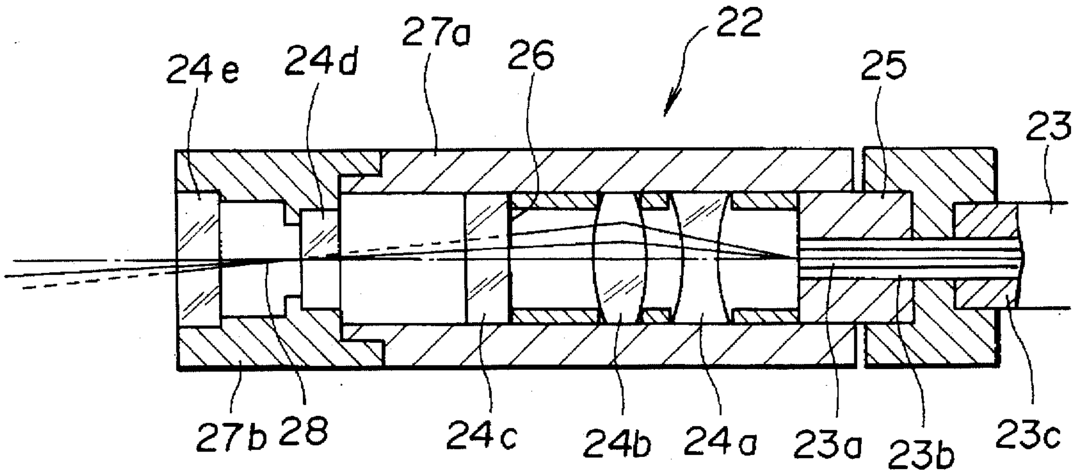
FIG. 4A is a planar cross-sectional view of a laser-line projection part which is provided on the endoscope distal-end part.
Figure 4B:
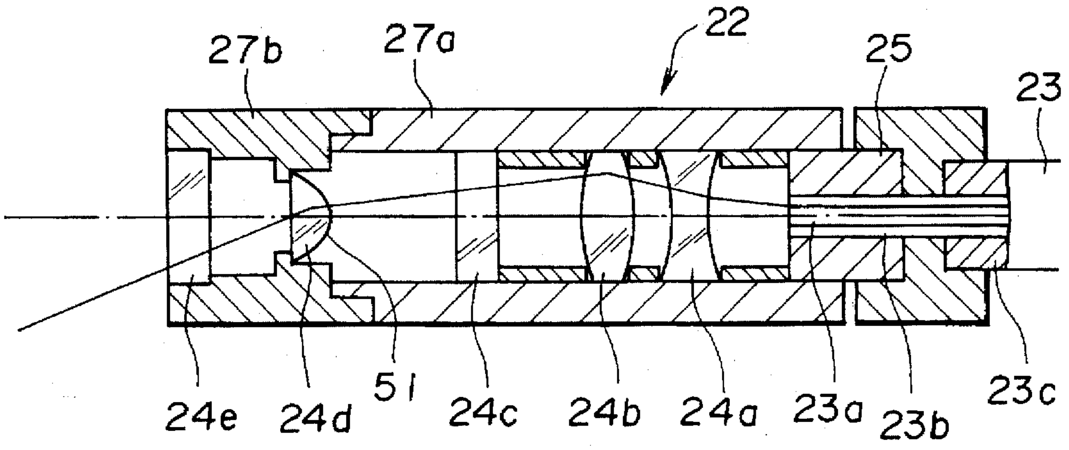
FIG. 4B is a side cross-sectional view of the laser-line projection part.
Figure 4C:
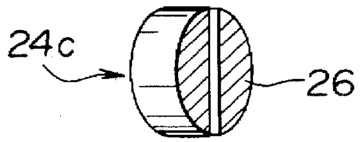
FIG. 4C is a view showing construction of a parallel planar plate which is used in the laser-line projection part.

FIG. 4A is an enlarged view of the laser-line projection part 22 in FIG. 3. Furthermore, FIG. 4B is a cross-sectional view as viewed from a side surface of FIG. 4A. FIG. 4C is a detailed view of a parallel planar surface plate 24*c* which is used in FIGS. 4A and 4B. The optical fiber 23 comprises a core part 23*a* having a large or high refractive index, for example, a clad part 23*b* having a refractive index lower than that of the core part 23*a*, and a jacket part 23*c* for protecting these parts. The laser light is transmitted by the core part 23*a* while being fully reflected by a boundary surface between the core part 23*a* and the clad part 23*b*.

The output light which is outputted from the distal-end surface of the optical fiber 23 which is held or retained by a base 25 is formed to a desirable luminous flux by lenses 24*a* and 24*b*. Thereafter, the output light passes through a parallel planner plate 24*c*, and is incident upon a cylindrical lens 24*d* having a convex surface 51, as shown in FIG. 4B. The output light ray from the cylindrical lens 24*d* is fan-shaped or sector-form broadening or spreading, as shown in FIG. 4B, and is outputted forwardly through a cover glass 24*e*.

As shown in FIG. 4C, a slit-like stop or diaphragm 26 is formed on the parallel planner plate 24*c* by means of evaporation or deposition or the like. The slit-like stop 26 is arranged such that, in FIG. 4C, a light-blocking film is formed on a portion which is indicated by oblique lines or slashes so as to become a slit-like opening through which the light is made transparent in upward and downward directions, and, in FIG. 4A, a longitudinal direction of the slit-like opening becomes a vertical direction with respect to the sheet of paper.

The parallel planer plate 24*c* is adhered to a lens frame 27*a*, and the cylindrical lens 24*d* is adhered to a lens frame 27*b*. The lens frame 27*a* and the lens frame 27*b* are adhered and are fixed such that the longitudinal direction of the opening in the slit-like stop 26 is the parallel planar plate 24*c* is made coincident with the spreading direction of the light of the cylindrical lens 24*d*.

In this manner, it is possible to narrow or reduce a line width as shown in FIG. 4A by the provision of the slit-like stop 26, without the spreading direction of the laser light shown in FIG. 4A by the provision of the slit-like stop 26, without the spreading direction of the laser light shown in FIG. 4B being narrowed or reduced. Specifically, as shown in FIG. 4A, only the laser light which is inputted to the parallel planer plate 24*c* with a small angle with respect to an optical axis passes through the opening in the slit-like stop 26, and the laser light which is inputted with a large or high angle is blocked. Thus, it is possible to reduce the line width. Meanwhile, as shown in FIG. 4B, since light blocking is not conducted with respect to the longitudinal direction of the slit-like opening, the arrangement is such that a line length of the laser line which is projected onto the object can increase or can be lengthened.

It is desirable that the above-described slit width is on the order of 0.2 mm. If the slit is greater than that, the line width increases or is thickened, and resolution of the measurement is reduced. Conversely, if the slit width is reduced to be less than that, the line width increases by affection or influence of diffraction. The resolution of the measurement is also reduced.

Further, it is preferable that a position where the parallel planar plate 24*c* provided with the slit-like stop 26 is arranged is far away from a pupil position 28, as shown in FIG. 4A. This is because there are no effects of the stop, at a location adjacent to the pupil position 28.

Moreover, the convex surface 51 of the cylindrical lens 24*d* is arranged so as to become the side of the optical fiber 23. Thus, an amount of generation of spherical aberration is reduced so that it is possible to increase the spreading of the light ray. Specifically, there are advantages such that the intensity of the laser line which is projected onto the object surface 15 is uniform so as to be able to project the length of the laser line a long distance.

Moreover, it is desirable that the optical fiber 23 is a single mode fiber. In case where a multi-mode fiber is used, there is the following advantage. Specifically, incident efficiency upon the fiber of the laser is improved, but there exist a plurality of modes in transmission of the light. The plurality of modes interfere with each other so that intensity nonuniformity is generated in the output light of the fiber. For this reason, the intensity nonuniformity is generated in the light which is projected onto the object surface 15.

Figure 5A:
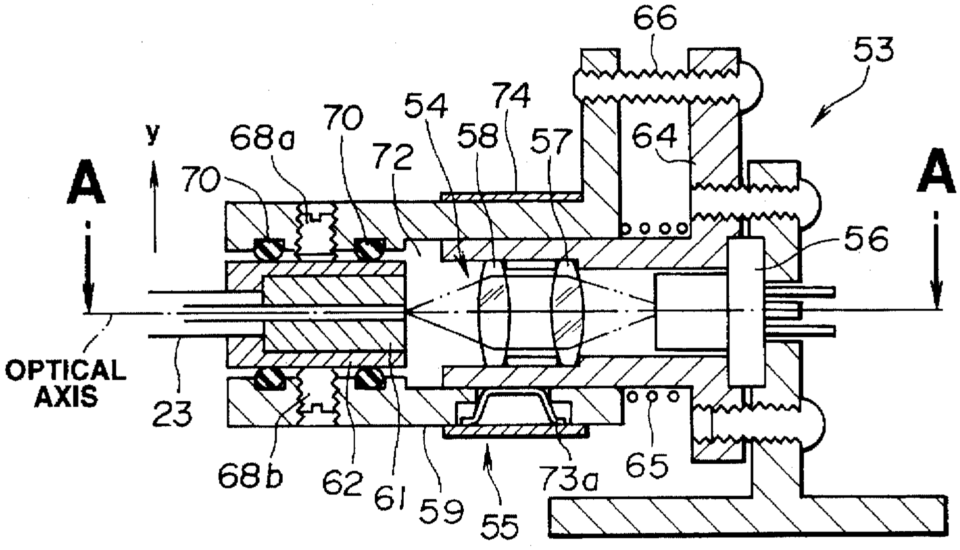
FIG. 5A is a cross-sectional view of a laser-line light source which is provided with a jogging mechanism of a base.
Figure 5B:
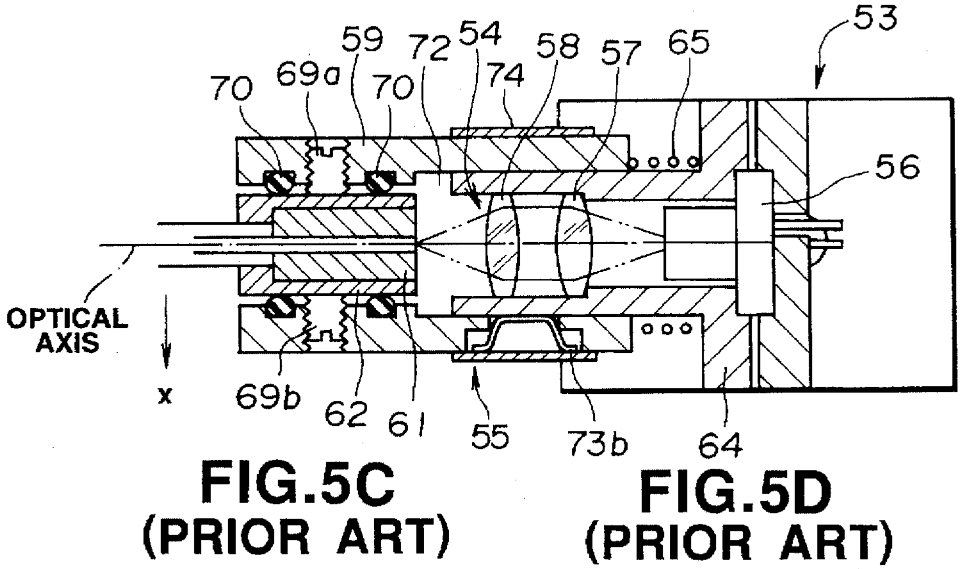
FIG. 5B is a cross-sectional view taken along a line A—A in FIG. 5A.

FIG. 5A and FIG. 5B show a cross-section including a y-axis of a laser light-source unit 53 which resides within the laser light source 5, and a cross-section including an x-axis. The laser light-source unit 53 is formed by a light emission part 54 and a light receiving part 55 which has a movement mechanism with respect to the light emission part 54. The light emission part 54 is formed by a laser diode 56, a collimator lens 57 for making the light of the laser diode 56 a parallel light ray, and a condenser lens or a converging lens 58 for conducting conversion to a fiber end face.

The light receiving part 55 is formed by a body 59, a base 61 of the optical fiber 23, and a base receipt 62. The body 59 receives pressure in a z-direction by a thrust urging spring 65, with respect to a frame 64 of the light emission part 54. Reaction force thereof is received by the z-direction jogging screw 66. The z-direction jogging screw 66 is rotated whereby the body 59 is moved in the z-direction.

By this regulation, the light of the converging lens 58 is converged to the fiber end face. Furthermore, the base receipt 62 is supported by y-direction jogging screws **68*a* and 68*b* and x-direction jogging screws 69*a* and 69*b*. Thus, the fiber end face is movable in a direction (x, y) perpendicular to the optical axis. Further, the base receipt 62 is supported by O-rings 70. The base receipt 62 serves as an urging spring for the jogging screws 68*a*, 68*b*, 69*a* and 69*b*, and prevents waste material from entering a space 72**.

Further, in the present embodiment shown in FIG. 5A and FIG. 5B, a pair of urging springs **73*a* and 73*b* for urging the frame 64 of the light emission part 54 from a radial direction are provided on the body 59, to remove backlash. A cap 74 is covered on the outward side of the urging springs 73*a* and 73*b*. Generally, a core diameter of the optical fiber is a few μ to a few ten μ. Adhesion of the waste material to the end face thereof forms critical or fatal loss of quantity of a light. Like the present embodiment, the urging member of the jogging screws is conducted by the O-rings 70**, whereby it is possible to cause the present embodiment to be dust proof in which waste material is prevented from being adhered to the fiber end face by inferior construction.

Figure 5C:
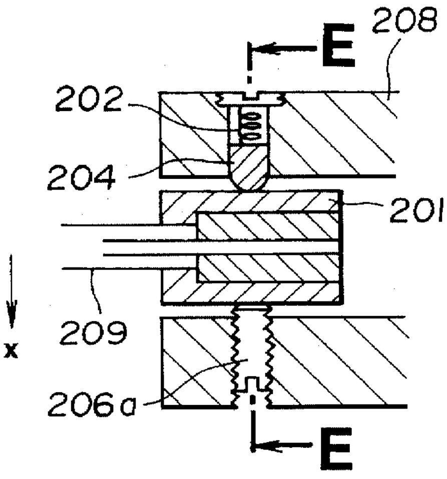
FIG. 5C is a cross-sectional view showing a jogging mechanism of a base in the prior-art example for comparison.
Figure 5D:
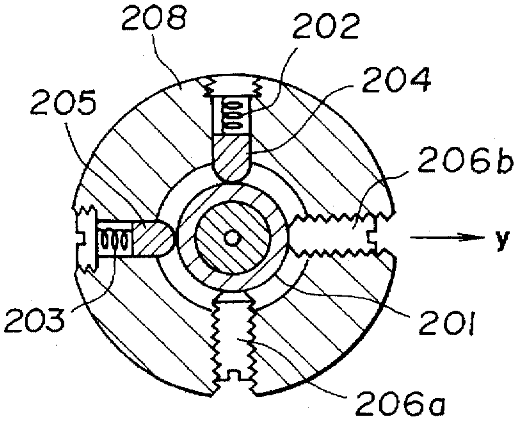
FIG. 5D is a cross-sectional view taken along a line E—E in FIG. 5C.

For comparison, FIG. 5C and FIG. 5D show a prior-art example of an x- and y-direction jogging mechanism. FIG. 5D shows a E—E cross section of FIG. 4C. A base receipt 201 is urged by plungers 204 and 205 which are urged respectively by urging elements, and urging springs 202 and 203, for example. Jogging screws **206*a* and 206*b* are provided at positions which are opposed respectively against the plungers 204 and 205 so that the jogging screws 206*a* and 206*b* can jog the base receipt 201 in the x- and y-directions. In this construction, since a gap is formed between the base receipt 201 and a frame 208, such a problem occurs that the waste material adheres to an end face of a fiber 209**. Moreover, since an urging mechanism is required, construction is large-sized, and the cost also increases.

In contrast, in the present embodiment shown in FIG. 5A and FIG. 5B, the urging element for the jogging screw is constituted by the O-rings 70, and invasion by the waste material is prevented by small and low-cost construction.

In place of the laser diode 56 shown in the present embodiment, an LED may be used (which emits a light of color such as red or the like, or which emits a light of wavelength of 600–700 nanometers). The laser diode 56 may be an emitter of a small-sized electrical bulb or an electrical lamp of construction which emits a red light, or the like.

Figure 6:
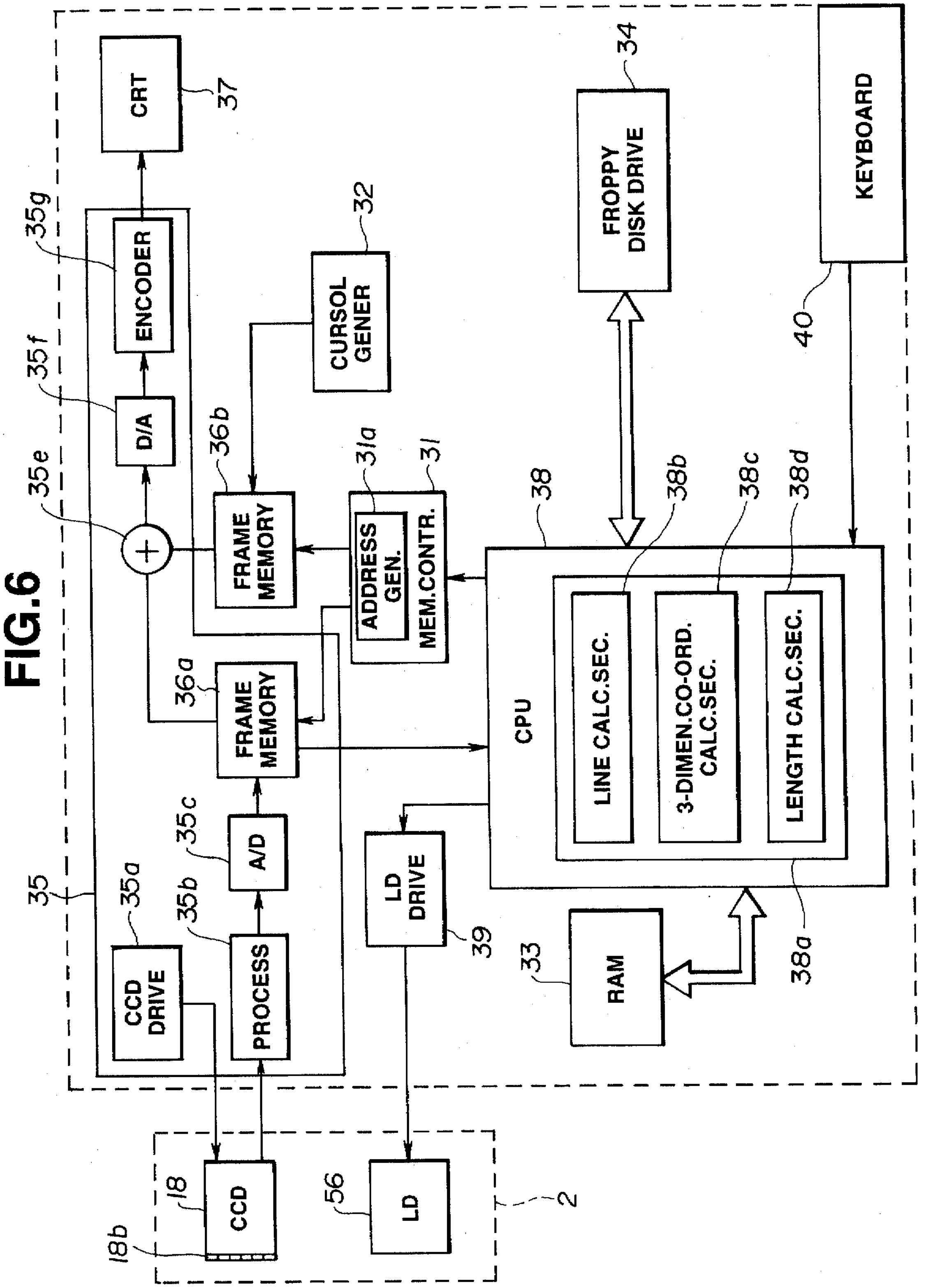

FIG. 6 shows a schematic arrangement of a signal processing system of the endoscope apparatus 1. The CCD 18 which is built in the electronic endoscope 2 is driven by a CCD drive signal from a CCD drive circuit **35*a* within a camera control unit (hereinafter abbreviated as 35. By the drive signal, an image-pickup signal which is outputted from the CCD 18 is processed by a process circuit 35*b* within the CCU 35**. Thus, an image signal having color-signal component of R, G and B, for example, is generated.

The image signal is converted into digital image data by an A/D converter **35*c* and is written to a frame memory 36*a*. The frame memory 36*a* is such that writing/reading thereof of the image data is controlled by a memory controller 31. The image data which are read out from the frame memory 36*a* pass through an adder 35*e*, and are converted into an analog image signal by a D/A converter 35*f*. Moreover, a synchronization signal SYNC or the like is added thereto by an encoder 35*g*, for example, so that the analog image signal is converted to a standard color image signal. The standard color image signal is outputted to a CRT 37 which serves as image display means. An endoscope image which serves as image which is image-picked up by the image pickup part 19 is displayed on a display surface of the CRT 37**.

Furthermore, a cursor generation circuit 32 which uses a character generator or the like is arranged within the measurement unit 4. It is possible to write a cursor of a cruciform or the like (+ or × or *) which is generated by the cursor generation circuit 32, to an optical position of a frame memory **36*b* through the CPU 38 by operation of a keyboard 40**.

The frame memory **36*b* is formed by a semiconductor memory having construction the same as that of the frame memory 36*a*. The cursor which is written to the frame memory 36*b* is read out together with the image-picked-up image which is written to the other frame memory 36*a*. The cursor is added by the adder 35*e*, and is displayed on the display surface of the CRT 37** is superimposition.

Accordingly, the present embodiment has a cursor display function which displays the cursor on the display surface. The writing and reading-out of the cursor are controlled by the CPU 38 through the memory controller 31. In the case where the CPU 38 conducts the length measurement, the CPU 38 refers to a position of the cursor which is written to the frame memory 36 to conduct calculation or the like of the coordinate value of an assignment point or the like which is assigned to the image.

Specifically, the frame memory which stores the image in the frame memories **36*a* and 36*b* is the frame memory 36*a*, and is the same in construction as the frame memory 36*a*. The frame memory which stores the cursor is the frame memory 36*b*. Both the memories are accessed by an address signal from the same address-signal generation circuit 31*a***.

For example, upon normal reading out, the stored data of both frame memories **36*a*, 36*b* are successively read out by the same address signal. Accordingly, both the stored data which are read out by a memory cell of the same address are displayed on the same position on the CRT 37**.

Further, when an operation is conducted which moves the cursor from the keyboard 40, the cursor, for example, is moved on the frame memory **36*b* under the control of the CPU 38. Together with the movement, the cursor which is displayed on the display surface of the CRT 37 is also moved. Accordingly, the coordinate of the point on the image which is assigned by the cursor, on the display surface of the CRT 37 corresponds to the address on the frame memory 36. Thus, the coordinate position of the cursor is identified by the address. In the case of the length measurement, the cursor is moved to an optional position on the image, and an address thereof is read out, whereby the CPU 38** calculates the coordinate position thereof.

Moreover, the respective frame memories can independently be written, read out or erased by a select signal or the like which selects the individual frame memories. Accordingly, the present embodiment has cursor display function which displays the cursor on the display surface, and a function which reads out the coordinate of the cursor on the frame memory 36*b* .

Furthermore, the CPU 38 conducts calculation or the like of a three-dimensional coordinate of a point which is assigned in position, by positional assignment by means of the cursor, or the like, with respect to the image which is displayed on the CRT 37, to conduct processing of measurement computation or operation of depth calculation of a recess to be described subsequently. Specifically, the CPU 38 has processing function of a measurement operation part (or length measurement operation part) 38*a* which calculates the depth of the recess or the height of the projection.

More specifically, the function of the measurement operation part 38*a* is formed by a line calculation part 38*b* for conducting calculation of a three-dimensional mathematical expression of a standard line, a three-dimensional coordinate calculation part 38*c* for conducting the three-dimensional coordinate of the measurement indication point upon which the measurement in the recess is assigned, and a length calculation part 38*d* for calculating a length of a perpendicular which is taken down from a measurement indication point to the standard line.

In the case where the CPU 38 conducts processing of the measurement operation part 38*a*, the CPU 38 reads out data (a value of H, or the like) required for calculation, which are recorded on a floppy disc 34, for example. The CPU 38 temporarily stores the data in a data storage area of a RAM 33, and refers to the data and conducts operation (calculation) for measuring a depth, a height or the like. A part of the RAM 33 is used as a work area to conduct the operation. The arrangement is such that values of the calculated depth or the like can be recorded on the floppy disk 34.

In the present embodiment, the laser diode 56 that is the light source for the laser line is used whose wavelength is 600–700 nanometers, for example, whereby the laser line which is projected onto the object surface can be identified with good contrast from the object surface. If the wavelength becomes greater than 700 nanometers, the laser line is attenuated by an infrared cut filter which is normally used in an image pickup optical system of an endoscope, so that it becomes impossible to conduct image pickup.

In connection with the above, in the case where the infrared cut filter is arranged on the side of the illumination light source or on the side of an optical system which outputs an illumination light within the endoscope, it is possible to use a laser diode which outputs a laser light whose wavelength is greater than 700 nanometers.

Further, by the fact that the wavelength is equal to or more than 600 nanometers, it is possible to control light-emission luminous intensity of the laser diode 56 from a signal intensity or strength of red as follows:

The CPU 38 reads out the signal intensity of red from the frame memory 36*a*. The CPU 38 sends an indication to a laser diode drive circuit 39 such that the CCD 18 becomes a level which is not saturated, and conducts control of the quantity of a light of the laser light or the light-emission luminous intensity thereof.

Generally, the pipe inner surface which serves as a principal measurement object in the present embodiment is contaminated by stains, adhesive matters or the like so that a reflective index is lowered. However, the red light is relatively superior in contrast so that it is possible to identify the red light. Moreover, since a red semiconductor laser which outputs the laser red light is such that one which is high in optical output is available at low cost, the semiconductor laser is used whereby it is possible to reduce the cost of the system or the endoscope measurement apparatus 1.

The CPU 38 conducts calculation processing of the length measurement to be described subsequently, by input of the measurement indication from the keyboard 40.

Figure 8:
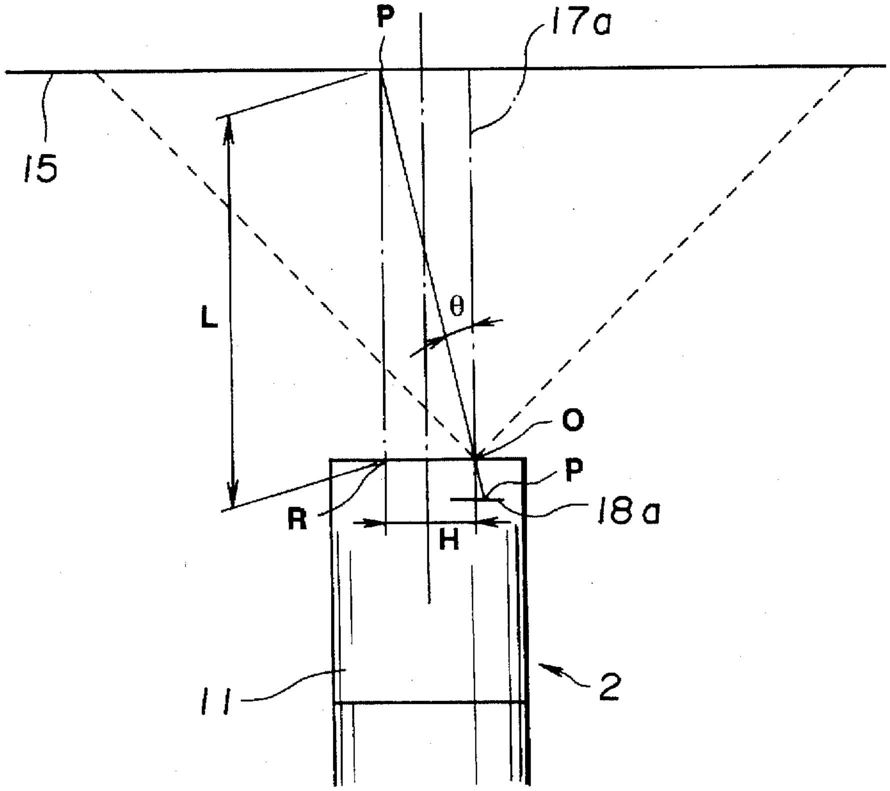

FIG. 7 and FIG. 8 show the principle of measurement.

As shown in FIG. 7, the sector-shaped light which is outputted from the laser-line projection part 22 describes the laser line 41 on the object surface 15. FIG. 8 shows a B—B cross-section of FIG. 7. Broken lines in FIG. 8 show a visual field range. It is assumed that an incident pupil position of the object lens system 17 is O, an outputting position of the laser-line projection part 22 is R, and a point on the laser line 41 which is projected onto the object surface 15 and with the B—B cross-section is P. Furthermore, it is assumed that an angle which is formed by a optical axis 17*a* of the object lens system 17 and O-P is θ. If it is assumed that a distance R-P from the laser-line output position R to the object surface is L, L can be found from a distance H of O-P and the product of tan(90-θ), that is, $$L = H \times \tan(90-\theta) \qquad (1)$$

In FIG. 8, the point P is image-formed at a point p on the image pickup surface 18*a* of the CCD 18.

Figure 9:
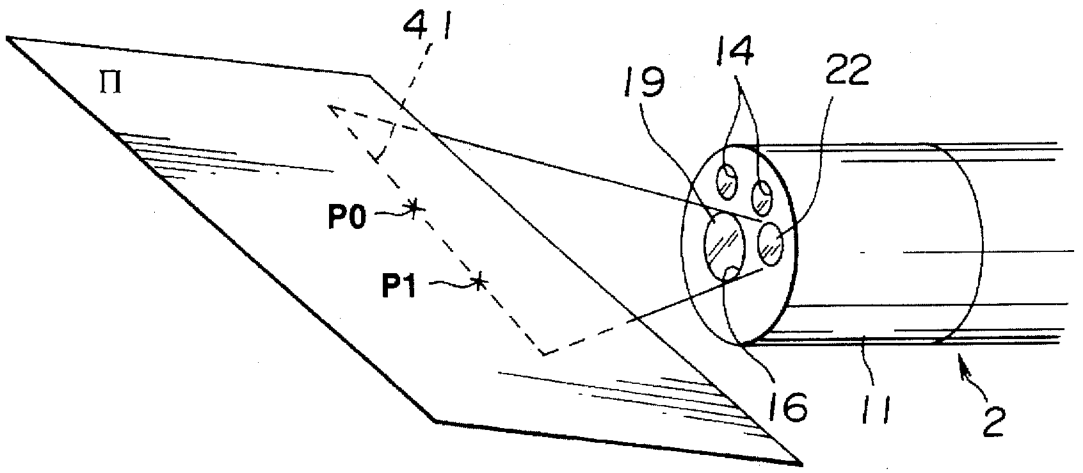
Figure 10:
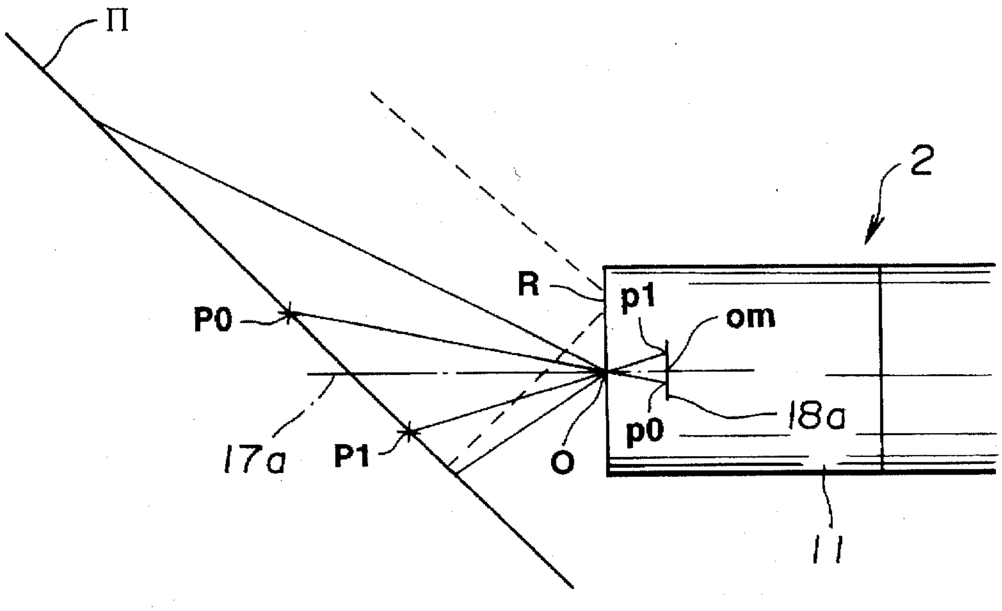
Figure 11:
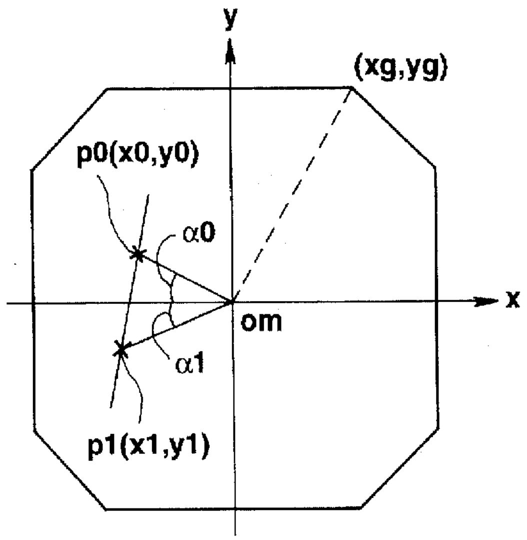
Figure 12A:
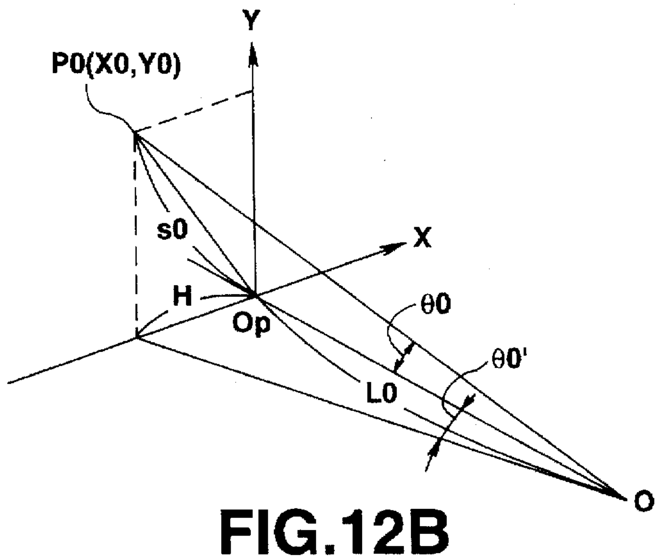
FIG. 12A and FIG. 12B are explanatory views showing the relationship between the measurement point and the optical system.
Figure 12B:
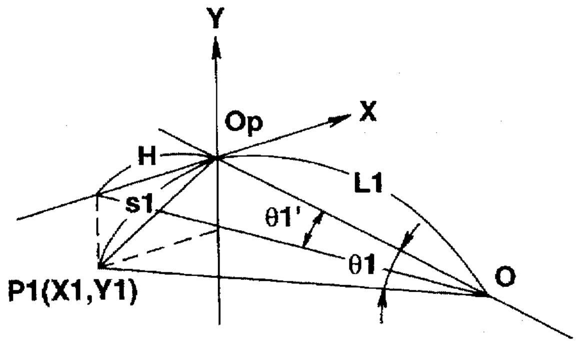

FIG. 9 shows a state in which the laser line 41 is projected onto an oblique plane. FIG. 10 is a side elevational view thereof. FIG. 11 shows an image in which measurement points P0 and P1 on the laser line 41 in FIG. 9 or FIG. 10, for example, are image-picked up, on the frame memory 36*a* (or 36*b*), for example. Moreover, FIG. 12A and FIG. 12B are explanatory views for finding a relational expression of the length measurement in case where an image-pickup optical system (in the present embodiment, the object lens system 17) is used so as to image-pick up the respective measurement points P0 and P1.

A coordinate system is set in which an indecent pupil position on a center axis (optical axis) of an image pickup optical system is made to the origin O of the three-dimensional coordinate. Furthermore, in order to facilitate understanding, a Z-axis of the three-dimensional coordinate is set in a direction of the optical axis, and a two-dimensional coordinate plane is moved on the optical axis so that the two-dimensional coordinate which is arranged on the side of a measurement point (that is, a plane including a measurement point P0 or P1) is indicated by (X, Y), and two-dimensional coordinate which is arranged on the image-pickup side (that is, on the image pickup surface 18*a* or the frame memory 36) is indicated by (x, y).

In this case, the origin Op on the side of the measurement point exists on a position which is moved through Z0 (in case of the point P0) or Z1 (in case of the point P1) from the origin O of the three-dimensional coordinate, on the optical axis, while the origin om on the image-pickup side exists on a position which is moved through the focal length f of the object lens system 17 from the origin O of the three-dimensional coordinate. Further, the x-axis and the X-axis, and the y-axis and the Y-axis are both in parallel with each other. Moreover, in the present embodiment, the x and the X coordinate is set in a direction in which the output position R and the origin O are tied to each other.

It is assumed that the image of the image-pickup surface 18*a* of the CCD 18 is stored in the frame memory 36*a* as it is. It is assumed that, for example, the center of the image pickup surface 18*a* is set so as to become the center of the frame memory 36*a*, and a position which is assigned by the same coordinate is a corresponding point. In this connection, in the case where both the positions are different from each other in unit or scale, a coefficient is multiplied upon one of them, or the like so that it is possible to conduct conversion to points which correspond to each other.

Accordingly, in a case where the measurement points P0 and P1 on the laser line 41 are image-picked up, a corresponding point on the frame memory 36 becomes p0 and p1.

Further, as shown in FIG. 12A, it is assumed that the coordinates of the measurement points P0 and P1 are made respectively to (X0, Y0) and (X1, Y1). As shown in FIG. 11, then, the coordinates of the corresponding points P0 and P1 on the frame memory 36*a* become respectively (x0, y0) and (x1, y1). Moreover, since the x-axis or the X-axis is set in the direction in which the output position R and the origin O are connected to each other, the lengths Op-X0 and Op-X1 in FIG. 12A become H.

It is assumed that an angle defined between a line by which the origin om and the measurement point (image of P0) p0 are connected to each other and the x-axis on the frame memory 36*a* is α0, and an angle defined between a line by which the origin om and the measurement point (image of P1) p1 are connected to each other and the x-axis is α1. It is assumed that the maximum angle of view of the image is θg, and the coordinate on the frame memory 36*a* is (xg, yg).

In a case where the image pickup optical system has distortion of SIN θ type, angles θ0', θ1', θ0 and θ1 are found shown in FIG. 12A and FIG. 12B by the following equations:

$$\theta 0' = \sin^{-1}\{x0 \times \sin(\theta g)/sqr(xg^2+yg^2)\},\ \theta 1' - \sin^{-1}\{x1 \times \sin(\theta g)/sqr(xg^2 \times yg^2)\},$$

$$\theta 0 = \sin^{-1}\{sqr(x0^2+y0^2) \times \sin(\theta g)/sqr(xg^2+yg^2)\},\ \theta 1 = \sin^{-1}\{sqr(x1^2+y1^2) \times \sin(\theta g)/sqr(xg^2+yg^2)\} \quad (3)$$

Here, the sqr($x0^2+y1^2$), for example, expresses the square root of ($x0^2+y1^2$).

Distances L0 and L1 to planes which respectively include the measurement points P0 and P1 respectively become:

$$L0 = H \times \tan(90-\theta 0'),$$

$$L1 = H \times \tan(90-\theta 1') \quad (3)$$

Moreover, the distance so between Op-P0 and the distance s1 between Op-P1 respectively become:

$$s0 = L0 \times \tan(\theta 0),$$

$$s1 = L1 \times \tan(\theta 1) \quad (4)$$

Furthermore, the angles α0 and α1 can be found by the following equation:

$$\alpha 0 = \tan^{-1}(y0/x0),$$

$$\alpha = \tan^{-1}(y1/x1) \quad (5)$$

Further, the three-dimensional coordinate of the measurement point P0 becomes as follows:

$$x0 = s0 \times \cos(\alpha 0) \quad (6)$$

$$Y0 = s0 \times \sin(\alpha 0)$$

$$Z0 = L0 \quad (8)$$

Moreover, the three-dimensional coordinate of the measurement point P1 becomes as follows:

$$X1 = s1 \times \cos(\alpha 1) \quad (6')$$

$$Y1 = s1 \times \sin(\alpha 1) \quad (7')$$

$$Z1 = L1 \quad (8')$$

The distance D between two points of the measurement points P0 and P1 can be found by the following equation:

$$D = \{(X0-X1)^2+(Y0+Y1)^2+(Z0-Z1)^2\}^{1/2} \quad (9)$$

Further, as will be described hereinafter, it will be required to find an expression of a line which three-dimensionally expresses a standard line to calculate a depth of a recess or the like. For this reason, in the case where the coordinates of two points which correspond to two points designated on the standard line are assumed to be P0 and P1, a straight line which passes through the two points P0 and P1 is given as follows:

$$(X-X0)/(X1-X0) = (Y-Y0)/(Y1-Y0) = (Z-Z0)/(Z1-Z0) \quad (10)$$

FIG. 13 shows an aspect in which a cylindrical-pipe inner surface 44 which serves as a measurement object is inspected by the endoscope 2. FIG. 13 shows a case where a recess 45 due to a wall-reduced part reduced in thickness by corrosion, for example, exists on the pipe inner surface 44 to measure a depth of the recess 45. For this reason, setting is made such that the recess 45 enters into an observation field of view or an observation visual field, and the distal-end side of the endoscope 2 is moved, the curvature part 12 is curved, or the like such that a laser line 46 projected onto the pipe inner surface 44 passes through the recess 45.

At this time, the direction of the laser line 46 is coincident with the axial direction of the pipe to reduce the measurement error. Furthermore, the laser line 46 passes through the measurement point C which intends to conduct measurement of the depth of the recess 45, and is projected upon the pipe inner surface 44 so as to extend on a reference surface which serves as the reference of the depth measurement (that is, the depth is zero). It is assumed that portions of the laser line 46 which are projected on the reference surface are P2 and P3. In this case, as shown in FIG. 13, it will be unnecessary to set the distal-end surface of the endoscope of direct vision type parallel to the pipe inner surface 44. The state may be a state to conduct observation (or image pickup) obliquely.

Reference points of measurement A and B are taken by the keyboard 40 on portions P2 and P3 of the laser line 46, and the measurement point C in which the depth is desired to be measured is indicated. The endoscope image (on the frame memory 36*a* or which is displayed on the display surface of the CRT 37) which is acquired under this state becomes one indicated in FIG. 14.

As shown in FIG. 14, the image becomes an image in which an image of a laser line (laser-line image) 46' is piled upon an image of a recess (recess image) 45', and a line direction of the laser-line image 46' is coincident with the axial direction of the pipe. Further, the laser-line image 46' passes through the recess image 45', and extends on the reference surfaces on both sides thereof. Image portions corresponding respectively to P2 and P3 in FIG. 13B, that is, laser-line image portions on the reference surface become p2 and p3. Points on p2 and p3 which correspond respectively to two actual points A and B are a and b. A point on the image which corresponds to the measurement point C becomes c.

Setting procedure of the measurement, or the like, has been described with reference to FIG. 13B. In actuality, however, reference of the endoscope image in FIG. 14 or setting or assignment thereof in the image is conducted as follows. The CPU 38 conducts treatment or processing of the length measurement of the depth of the recess or the like as shown in a flow chart shown in FIG. 15, for example, in accordance with the setting and assignment thereof.

As shown in S1, setting of the laser line is made so as to pass through the recess. Specifically, a setting is made such that the laser-line image 46' passes on the recess image 45' (serving as the image of the measurement object) within the image which is displayed on the CRT 37. In this case, the side of the distal end of the electronic endoscope 2 is moved, is curved or the like such that the line direction of the laser-line 46' is made parallel to the axial direction of the pipe.

Subsequently, as shown in Step S2, assignment of points which serve as the two references within the image is conducted by the cursor. Specifically, in order to set the reference line which serves as the reference of the measurement, the cursor is moved to a position having no irregularity, on the line of the laser-line image 46', and assignment points a and b that serve as the two references are assigned.

Subsequently, as shown in Step S3, three-dimensional coordinates of the actual reference points A and B which correspond respectively to the points a and b are calculated. Specifically, if the two assignment points a and b are assigned, the CPU 38 calculates the three-dimensional coordinates of the actual reference points A and B which correspond respectively to the points a and b, by the relational expression or relation of the triangulation.

Moreover, as shown in Step S4, a straight line which passes through the reference points A and B is calculated. The CPU 38 calculates the three-dimensional coordinates of the actual reference points A and B and, thereafter, further calculates the mathematical expression of the three-dimensional straight line which passes through the reference points A and B by the following expression (10').

Subsequently, as shown in Step S5, a point c is assigned on the recess, by the cursor. Specifically, the cursor is moved to a position of a point where the depth is intended to be measured on the line of the laser-line image 46' which passes through the recess image. The measurement assignment point c is assigned.

Then, by assignment of the measurement point c, the CPU 38 calculates three-dimensional coordinate of a measurement point C which corresponds to the point c, as shown in Step 86.

Subsequently, as indicated in Step S7, a length K of the perpendicular which lowers from the measurement point C is found from the following expression (12) with respect to the straight line. Specifically, a depth of the measurement point C (from the reference surface) is calculated.

The above-described processing contents will hereunder be supplementarily described.

Under a state set like FIG. 13 or FIG. 14, the three-dimensional coordinates (Xa, Ya, Za), (Xb, Yb, Zb) and (Xc, Yc, Zc) of the actual points A, B and C which correspond respectively to the two reference assignment points a an db and the measurement assignment point c for deciding or determining the straight line which serves as the reference can be found from calculation expressions which are indicated by the expressions (1)–(8).

Specifically, it is assumed that, in the expressions of (1)–(8) (and numbers to which ' is applied), the respective coordinates of the points A, B and C are the coordinate of P0 or P1 (corresponding thereto, it is assumed that the coordinates of a, b and c which correspond respectively to the points A, B and C are regarded also as the coordinates of p0 and p1), whereby it is possible to find the coordinates thereof.

Calculation of the coordinates of the points A, B and C is such that commands of the coordinate calculation indication, or the like, are inputted from the keyboard 40, whereby the CPU 38 conducts the calculation by function of the measurement operation part **38*a***. If the two points a and b for determining the straight line are assigned by a program, A and B may be automatically calculated. Furthermore, the expression of the straight line thereof may also be calculated.

Further, the expression of the straight line which passes through the points A and B becomes the following expression (10') in which codes of the expression (10) are changed:

$$(X-Xa)/(Xb-Xa)=(Y-Ya)/(Yb-Ya)=(Z-Za)/(Zb-Za) \qquad (10')$$

The directional cosines l, m and n of the straight line of the expression (10') become the following expressions (11), if $$h=Xb-Xa,\ i=Yb-Ya \text{ and } j=Zb-Za$$

are used:

$$l=h/(h^2+i^2+j^2)^{2/1},$$

$$m=i/(h^2+i^2+j^2)^{2/1}, \text{ and}$$

$$n=j/(h^2+i^2+j^2)^{2/1} \qquad (11)$$

As has been known well from the triangulation or the like, the length K of the perpendicular which lowers along a straight line in the expression (10'), from the point C becomes as follows:

$$K^2=(Xc-Xa)^2+(Yc-Ya)^2+(Zc-Za)^2-\{1(Xc-Xa)+m(Yc-Ya)+(Zc-Za)\}^2 \qquad (12)$$

It is possible to find K as the depth of the recess 45 which is desired to be found in this manner (In this connection, in FIG. 14, the length corresponding to the length (depth) K in FIG. 13 is indicated by k).

Figure 15A:
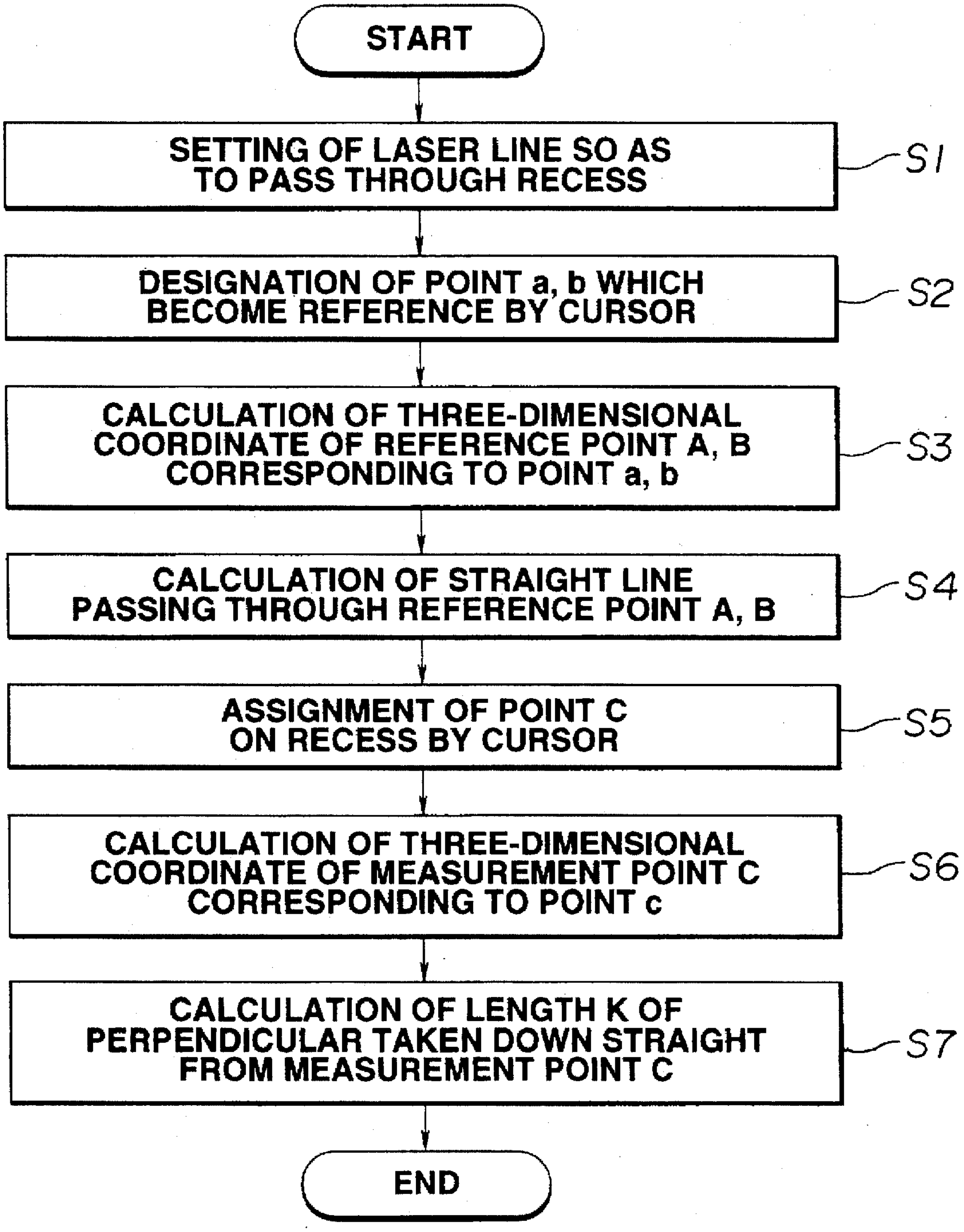
FIG. 15A is a flow chart showing the processing contents which calculate a depth of the recess.
Figure 15B:
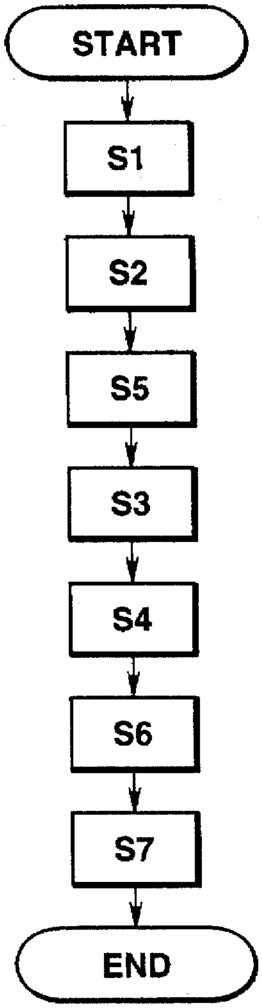

In connection with the above, processing of the length measurement should not be limited to the above-described order of Steps S1–S7. For example, as shown in FIG. 15B, Steps S3 and S4 may be carried out after S5. Specifically, the processing may be carried out in the order of S1, S2, S5, S3, S4, S6 and S7, to calculate the depth of the recess.

Figure 15C:
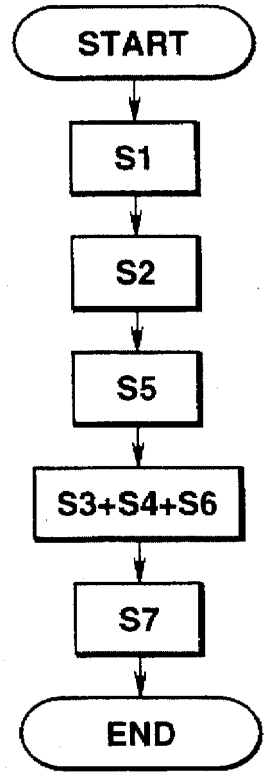

Moreover, the arrangement may be such that, in FIG. 15B, as shown in Steps, Steps S3, S4 and S6 are carried out together (this processing is shown in brief by S3+S4_S6) and are carried out as shown in FIG. 15C. In FIG. 15C, S4 is carried out after S3. However, S6 may be carried out before S3 or S4.

Figure 15D:
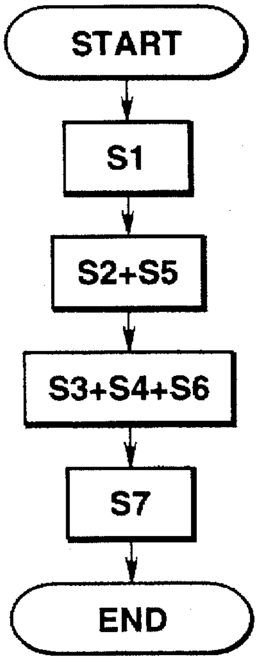

Furthermore, the arrangement may be such that, in FIG. 15C, Steps S2 and S5 are carried out together to carry out processing like FIG. 15D.

In brief, the arrangement may be such that the aforesaid Steps S1–S6 are replaced in order with each other to calculate the depth of the measurement point C.

FIGS. 13A and 13B show an example which finds the depth of the recess. However, it can similarly be conducted to find the height of the projection. In this connection, it will be clear that A and B are assigned to both the ends of the recess 45 whereby it is possible to find the length of the size of the recess 45 (from the expression (9)).

According to the first embodiment, even under the state in which the measurement object is observed from the oblique direction, it is possible to accurately find the depth of the recess, the height of the projection or the like due to the corrosion of the like of the pipe inner surface or the like.

In the present embodiment, even under the state in which the measurement object is observed from the oblique direction, it is possible to measure, in length, the depth of the recess and the height of the projection in or on the pipe inner surface of the like. However, the laser surface which is outputted from the laser-line projection part 22 to spread in the sector form is required to be a portion of the object surface (the pipe inner surface 44 in FIG. 13), upon which the laser line 46 is projected, and is required to be perpendicular to the object surface.

In order to be more easily understood, it is considered that the pipe inner surface is polygonal in shape, and the depth of recess which resides in a planar plate part thereof is measured. Then, it will be required in the case where accurate depth measurement is conducted that the state may be a state in which the recess is observed from the oblique direction, but the laser surface is perpendicular to the planar plate part.

A second embodiment of the present invention will subsequently be described with reference to FIG. 16 to FIG. 19.

In the principle of the measurement shown in the first embodiment, the arrangement has been such that the origin om of the frame memory shown in FIG. 11, the optical axis of the image pickup part 19 shown in FIG. 2 and the intersection of the image pickup surface (photoelectric conversion surface) 18a of the CCD 18, that is, the origin om are coincident with each other. The present embodiment is an embodiment in case where, even in the case where there is an optical variation, correction function correcting the optical variation is provided.

Figure 16:
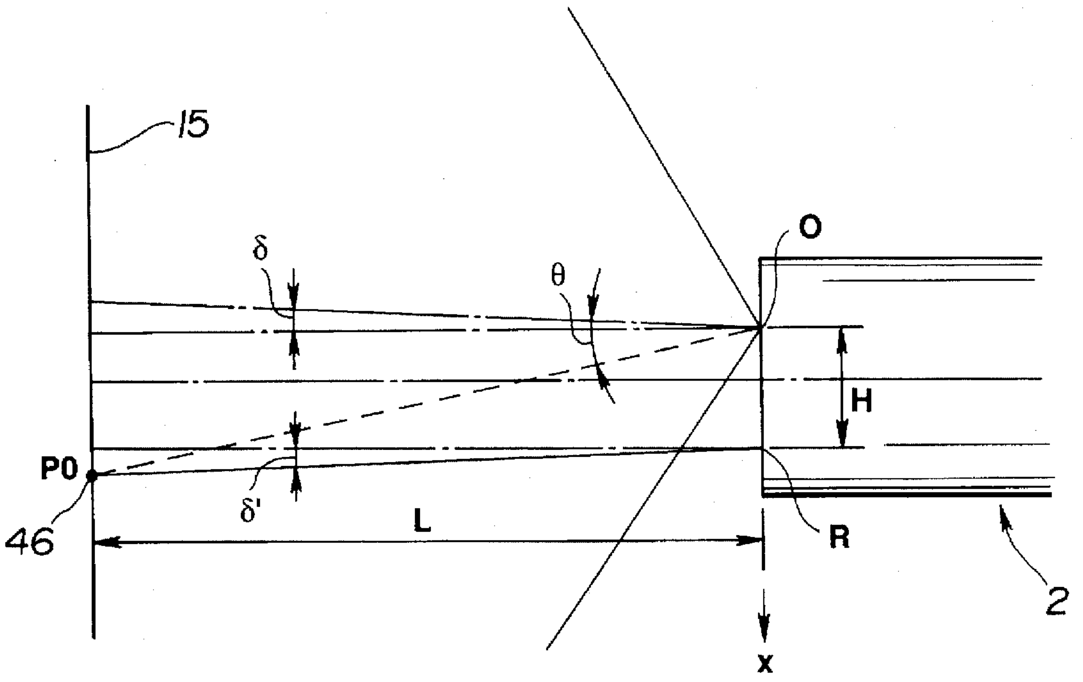
FIG. 16 is an explanatory view showing an aspect of case which is shifted optically.
Figure 17:
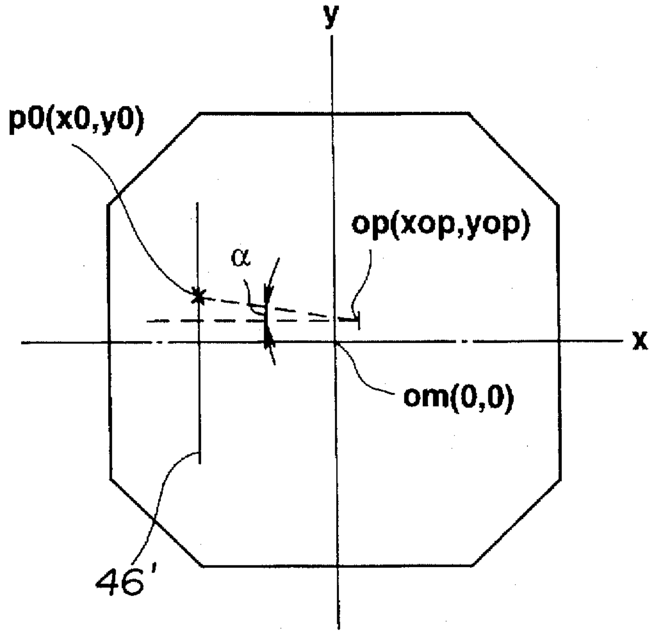
FIG. 17 is an explanatory view showing an image corresponding to that shown in FIG. 16, on a frame memory.
Figures 18, 19:
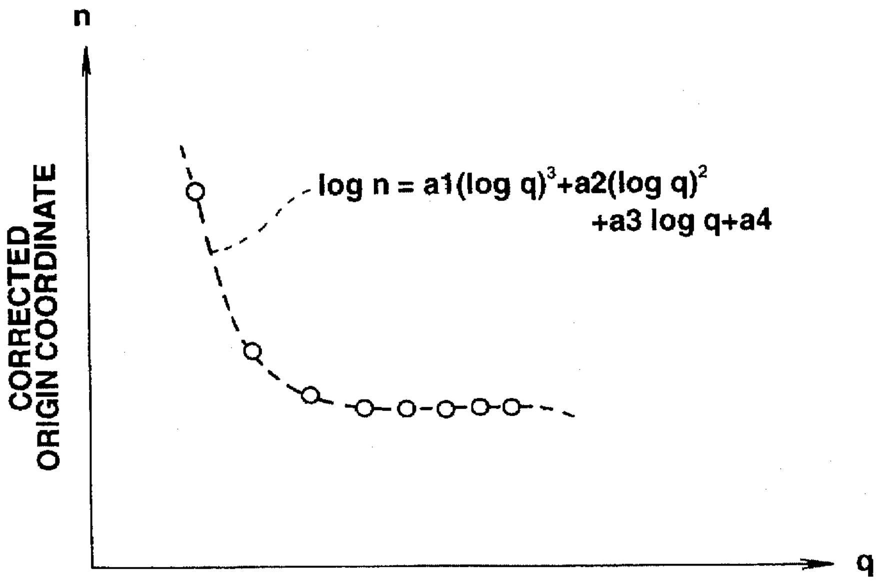
FIG. 18 is a table showing the relationship between an actual object distance and a corrected origin coordinate, in case of being shifted optically.
FIG. 19 is a graph showing an aspect in which the relationship of the table in FIG. 18 is approximated by an approximate equation.

FIG. 16 shows a state in which the direction of each of the optical axes and the direction of the center axis of the endoscope are shifted away from each other. FIG. 17 shows, in table, the coordinates on the frame memory, while FIG. 18 shows, in table, the relationship between the object distance which is calculated by the origin om, and the corrected origin coordinates. FIG. 19 shows that the relationship of FIG. 18 is shown by a graph, and can be approximated by the use of the corrected origin coordinates.

FIG. 16 shows the case where the axis of the electronic endoscope 2 and the optical-axis center of the image pickup system are shifted only by an angle $\sigma$ from each other, and the case where the axial direction of the electronic endoscope 2 and the laser line are shifted only by an angle $\sigma'$. In such a case, even if the expression (3) is utilized to calculate the object distance L to the point P0, H in the expression (3) varies depending on the object distance L. Accordingly, an error increases.

In view of the above, correction is conducted as follows, whereby it is possible to acquire an approximate value of the actual object distance L. Even if there exists a variation in the optical system, the approximate value is used whereby it is possible to calculate the depth or the height accurately.

FIG. 17 shows the center om on the frame memory and the optical-axis center op of the image pickup optical system, which correspond to those of case in FIG. 16. As shown in FIG. 17, it is assumed that the center om on the frame memory and the optical-axis center op of the image pickup optical system are shifted from one another.

In connection with the above, in FIG. 16, the laser line passes through the point P0, and extends in a direction perpendicular to the sheet of paper (an upper and down direction in FIG. 17, that is, in a y-axis direction). Moreover, in FIG. 16, the object surface 15 is shown under a state in parallel with the distal-end surface of the electronic endoscope 2.

Now, the case where the object distance L to one point P0 of the object is measured is considered. For this reason, definition is conducted as follows:

om: the origin (0, 0) of the coordinate system on the frame memory and set at a center thereof, op: optical-axis center coordinate ($x_{op}$, $y_{op}$) of the image pickup system on the frame memory, p0: coordinate (x0, y0) on the frame memory corresponding to the point P0, ks: distortion correction coefficients of the image pickup optical system, fe: coefficients for conversion to the image height on the frame memory, $\theta$: angle defined between the optical center of the pickup optical system and O-P0 (refer to FIG. 16), and $\alpha$: angle defined between the x-axis and op-p0 on the frame memory.

Further, px, py and r are defined as follows:

$$px=x_{op}-x0,$$

$$py=y_{op}-y0 \text{ and} \quad (13)$$

$$r^2=px^2+py^2 \quad (14)$$

Specifically, the length px of the x-coordinate component and the length py of the y-coordinate component from the optical-axis center of the point p0, and the length r to the point p0 are defined whereby the following relationships are found:

$$\alpha=\tan^{-1}(py/px) \quad (15)$$

$$\theta=ks\cdot\sin^{-1}(r/fc/ks) \quad (16)$$

$$L=H/(\cos\alpha\cdot\tan\theta) \quad (17)$$

The above-described value of L becomes the object distance with H serving as the reference. However, since the value of H is constant, the accurate object distance L cannot be calculated. An example of the calculation results in which, under this state (that is, assuming that H is constant, the known object distance L is changed), the expression (17) is used and it is shown on the table in FIG. 18. The first column of the table shows the actual object distance, and the second column shows the object distance from the origin op.

As will be understood from these numerical values, estrangement or alienation is formed in the object distance due to the origin op and the actual object distance, and a rate of the estrangement increases in the case where the distant is small. In view of this, the result in which calculation is made such that, in order to correct the variation or change of H, the origin op is so corrected as to become equal to the actual object distance is the corrected origin coordinate shown on the third column in a table of FIG. 18. If the object distance using the origin op and the corrected origin coordinate n are graphed, there can be provided FIG. 19. If an approximate expression is applied to the graph in FIG. 19, there can be provided the following expression:

q: object distance calculated on the basis of the origin op, and n: corrected origin coordinate Constants a1, a2, a3 and a4 are decided so as to satisfy the approximate expression as t due to $$\log n = a1\cdot(\log q)^3 + a2\cdot(\log q)^2 + a3\cdot(\log q)^3 + a4 \quad (18)$$

As the x-component of the corrected origin coordinate, the following is defined:

$$xc = 10(\log n) \quad (19)$$

If, on the basis of this result, the below-described expression (20) is used in substitution for the expression (13), and calculation of expressions (14)–(19) is conducted, there can be acquired values which are approximate to the actual object distance:

$$px = xc - x0, \text{ and}$$

$$py = yop - y0 \quad (20)$$

In this manner, since there can be acquired the values approximate to the actual object distance, it is possible to use expressions corresponding to the expressions (4)–(8), to decide the three-dimensional coordinate of the point P0. Moreover, since the other points can be similarly determined, it is possible to calculate the depth or the height as in the first embodiment.

In the present embodiment, the spreading direction of the laser light is coincident with the upper and lower direction of the image plane. Specifically, as shown in FIG. 17, the line direction of the laser-line image 46' is adapted to become parallel to the y-axis direction. Accordingly, in this case, the movement of the laser-line image 46' on the frame memory due to the change in object distance becomes only the x-axis direction.

Accordingly, the correction of the expression (20) may be limited to the x-axis direction and may be simple.

Thus, it is possible to reduce the number of calculations of the CPU 38 and the number of correction coefficients thereof. Furthermore, the fact that the distance H between the laser-line projection part 22 and the image pickup part 19 is high becomes large the field-of-view in the case where the irregularities are measured, and a resolution power of the measurement is improved. In the case where the outer diameter of the endoscope is limited, in order to make H larger or higher, if the laser line is projected perpendicularly to the straight line which connects the laser-line projection part 22 and the optical center of the image pickup system to each other, it is possible to take H to the largest or highest.

In the calculation expression of the present embodiment, the following parameters will be required for each scope:

op (xop, yop): optical-axis center coordinate on the frame memory, ks: distortion correction coefficients of the optical system, fc: coefficients for converting the actual image height to the image height on the frame memory, and a1, a2, a3, a4: coefficients of the approximate expression.

These parameters are found beforehand by measurement for every scope (electronic endoscopes). The parameters are recorded onto a recording medium such as a floppy disk or the like as information for correcting the found parameters. In the case where the parameters which are recorded onto the recording medium are inputted to the measurement unit 4, the arrangement may be such that the arrangement as shown in FIG. 20 is adopted whereby the information is read out through the floppy disk drive 34 which serves as a recording and reproducing device, for example, and is inputted to the CPU 38 which conducts calculation or operation of the correction.

Figure 20:
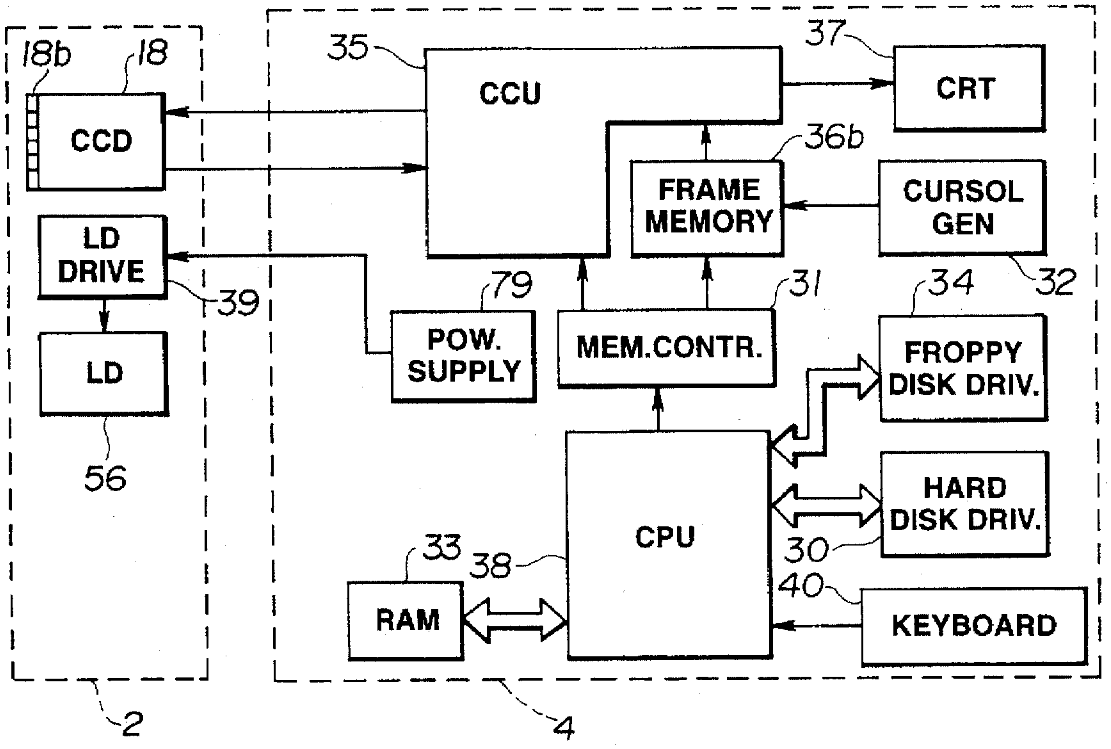
FIG. 20 is a block diagram of an electrical system in a second embodiment.

FIG. 20 shows the floppy disk drive (device) 34 and a hard disk drive (device) 30 which serve as an information recording and reproducing device which conducts measurement operation and correction operation due to the CPU 38. The above-described parameters are recorded onto the floppy disk drive 34 (the floppy disks which are recorded and reproduced by the floppy disk drive 34). Upon start of the use of the scope, the parameters are read into the CPU 38 from the floppy disk, and are recorded onto the hard disk drive 30. The parameters are referred to as occasion demands. The hard disk drive 30 records thereon the above-noted parameters, and the other parameters or data which are required for the measurement.

In the case where the same scope is repeatedly used, it is dispensed with only to refer to the hard disk 30. Accordingly, it is not necessary or unnecessary to repeatedly fetch the parameter from the floppy disk. In case where another endoscope for measurement is connected to the same measurement unit 4, a parameter is changed or replaced from the floppy disk.

As shown in FIG. 20, means for inputting the parameters which are required for measurement and which are varied for each endoscope, into the measurement unit 4 is provided. Accordingly, it is possible to conduct the measurement which is low in measurement error and which is superior in accuracy. Thus, it is possible to provide the measurement endoscope system or the endoscope measurement apparatus in which, even if the endoscope is changed or replaced, the measurement accuracy is not changed. The other advantages are the same as those of the first embodiment.

In connection with the above, the arrangement may be such that the parameters which are required for the measurement are recorded beforehand in the hard disk drive 30, and, in the case where an electronic endoscope which is not registered in the hard disk drive 30 is connected, the fact that the endoscope is not registered is displayed, and it is urged that the floppy disk in which the parameter is recorded is inserted.

In connection with the above, FIG. 20 shows the arrangement in the case where the LD drive circuit 39 is built in the electronic endoscope 2. Electric power which is required for operation of the LD drive circuit 39 is supplied from an electric source or power supply 79 which is built into the side of the measurement unit 4, through a power supply line.

A third embodiment of the invention will subsequently be described with reference to FIGS. 21–28.

Figure 22:
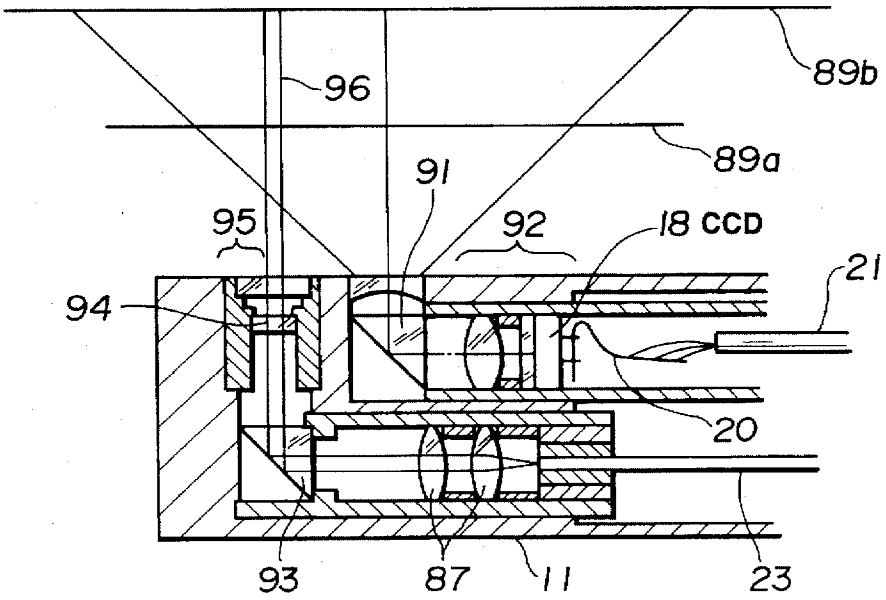
FIG. 22 is a cross-sectional view of a distal-end part of an electronic endoscope.
Figure 21:
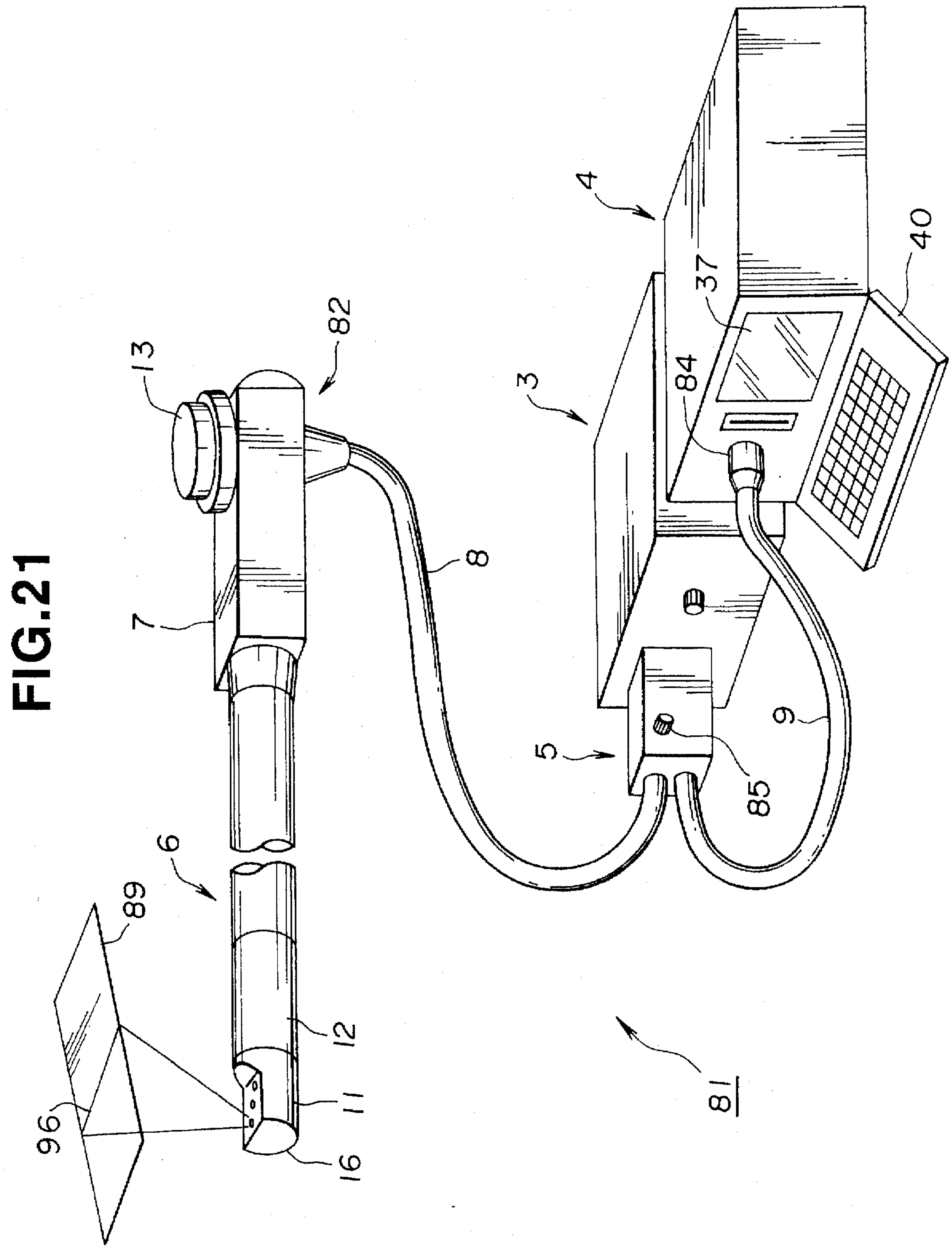
FIG. 21 is a whole arrangement view showing an endoscope apparatus according to a third embodiment of the invention.

As shown in FIG. 22, an electronic endoscope 82 according to the present embodiment is of side looking type which is arranged as follows. That is, the electronic endoscope 82 observes the side perpendicular to an axis of an insertion part. Further, the laser light source 5 is provided therein with a ROM 83 (refer to FIG. 23) serving as a semiconductor memory which records therein parameters required for measurement in case where the respective electronic endoscopes 82 are used. Access can be made from the CPU 38 within the measurement unit 4, through a CCU connector 84.

If the CCU connector 84 of the electronic endoscope 82 is connected to the measurement unit 4, a level of a terminal T1 which forms connection detection means is changed from "L" to "H", whereby the electronic endoscope 82 sends a connection signal which is connected to the measurement unit 4, to an interrupt terminal C1 of the CPU 38. On the basis of the connection signal, the CPU 38 reads out the parameters which are required for measurement, from the ROM 83. Thus, a measurement high in accuracy can be conducted by the correct parameters which are set with respect to the connected electronic endoscope 82.

Figure 23:
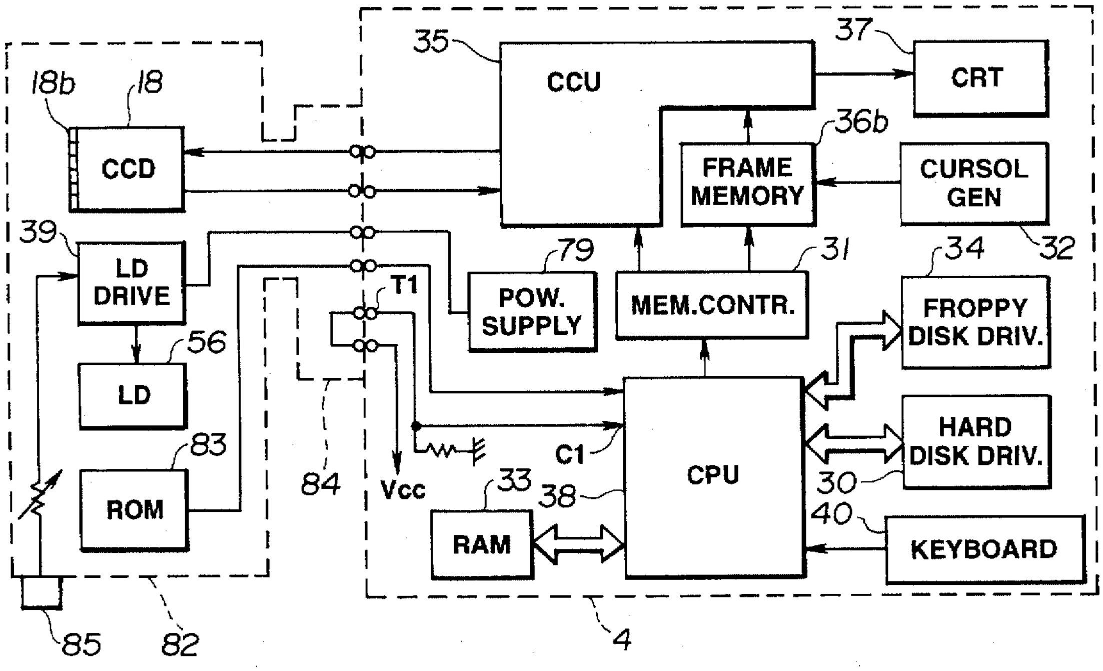
FIG. 23 is a block diagram of an electrical system of the endoscope apparatus.

As shown in FIG. 23, the laser diode 56 is driven by the LD drive circuit 39 which is provided with APC (automatic power control) function. A luminous intensity thereof can be adjusted by modification of a reference current value which decides the luminous intensity, for example, by a laser-line intensity knob 85.

Power supply to the drive circuit 39 is conducted from the power source circuit 79 within the measurement unit 4, through the CCU connector 84.

Figure 24A:
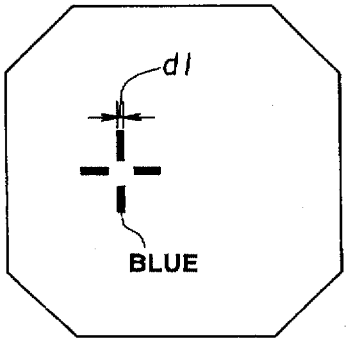
FIG. 24A and FIG. 24B are explanatory views showing a cursor on a CRT.
Figure 24B:
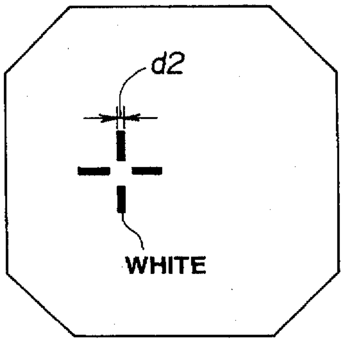

Moreover, as shown in FIG. 24A and FIG. 24B, it is possible to optionally vary the line width of the cursor displayed on the CRT 37, line d1 or d2, by indication from the keyboard 40. It is also possible to optionally change color thereof, like blue or white, by the indication from the keyboard 40.

As shown in FIG. 22, the endoscope has the distal-end part 11 thereof which has an image pickup system 92 of a side looking type which uses a first prism 91, and a laser-line projection part 95 which is bent laterally by a second prism 93 and which is spread in the form of a line by a cylindrical lens 94. A laser light which is transmitted by the optical fiber 23 is outputted from a distal-end face thereof. The laser light passes through collimation lenses 87 and becomes a parallel light ray. The laser light is bent laterally by the second prism 93. Furthermore, the laser light is spread into the form of a line by the cylindrical lens 94. The laser light passes through a cover glass and is projected onto an object surface 89*a* (or 89*b*) (In FIG. 21, the object surface is shown by 89).

A spreading direction of the laser light (or a direction of a laser line 96) which is outputted from the laser-line projection optical system 95 is set so as to be coincident with a left- and right-hand direction (lateral direction) of the image, as shown by 96' and 96" in FIG. 25, if shown on the image-picked-up image. The effects thereof due to the case of being set in this manner are substantially the same as those of the first embodiment.

Figure 25A:
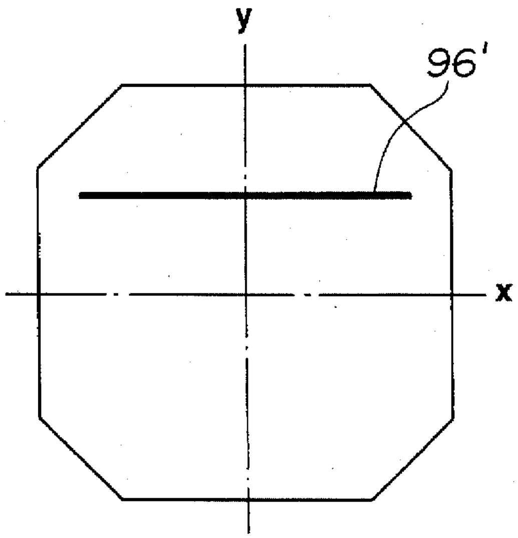
FIG. 25A and FIG. 25B are explanatory views showing movement of a laser line on the image.
Figure 25B:
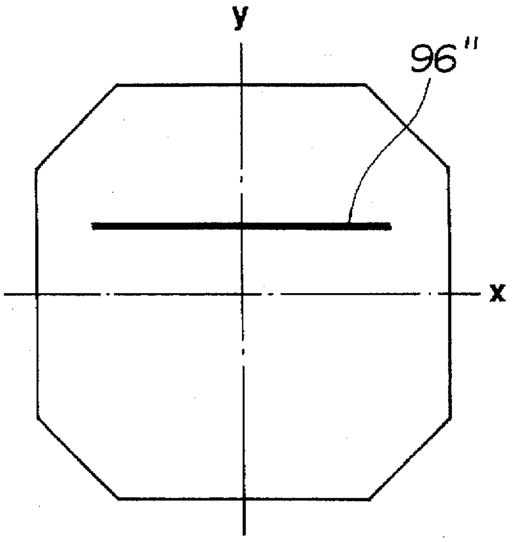

FIG. 25A shows an image in the case where an object distance is close or near, while FIG. 25B shows an image in case where the object distance is far away. Specifically, the image in the case of being projected on to the object surface 89*a* or 89*b* in FIG. 22 is shown in FIG. 25A and FIG. 25B. In this manner, the laser line 96' or 96" on the image is moved in the y-axis direction in accordance with the change in distance.

Figure 26:
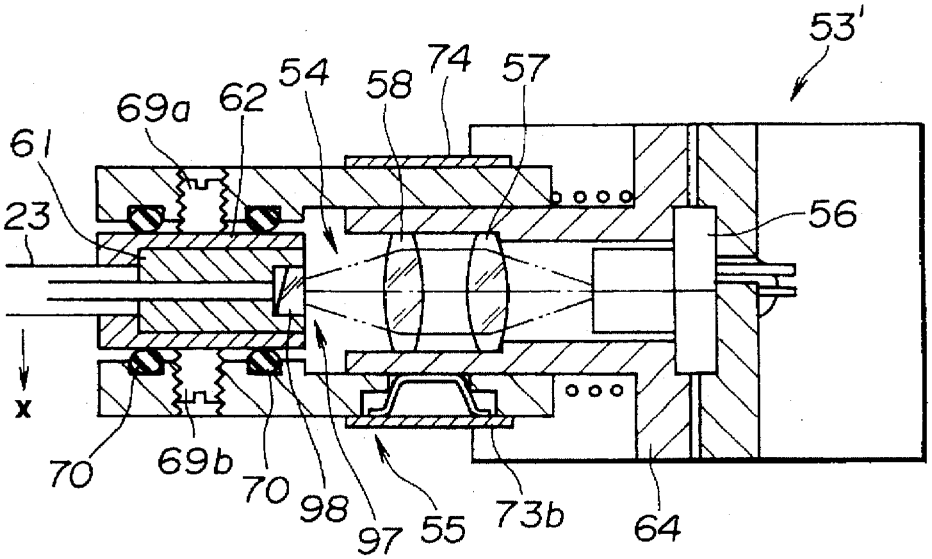
FIG. 26 is a cross-sectional view showing a laser light-source unit.

A laser light-source unit 53' in the present embodiment is of structure shown in FIG. 26.

Figure 27:
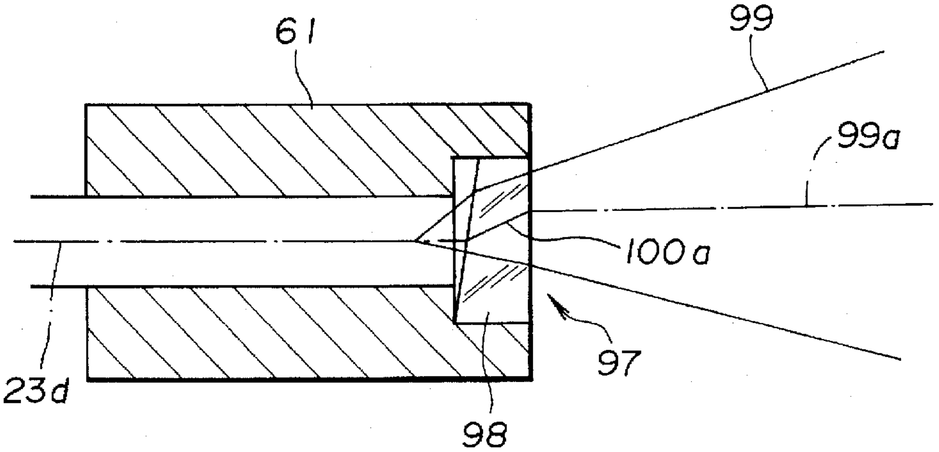
FIG. 27 is a cross-sectional view showing the details of an input part of an optical fiber in FIG. 26.

FIG. 26 corresponds to FIG. 5B of the first embodiment. A difference of the present embodiment from the first embodiment is that, as shown in FIG. 27, a wedge prism 98 is provided on an incident part 97 of an optical fiber 23. Operation of the wedge prism 98 will be described on the basis of FIG. 27.

On optical axis 99*a* of a laser light ray 99 is bent by the wedge prism 98 as shown by an optical axis 100*a*, and enters the optical fiber 23. The optical axis 100*a* is inclined with respect to a center axis 23*d* of the fiber 23, and the light ray enters obliquely the optical fiber 23. Since an incident angle of the light which is obliquely incident upon the optical fiber 23 is substantially preserved, the intensity distribution of the output light from the fiber 23 is changed or varies.

Figure 28:
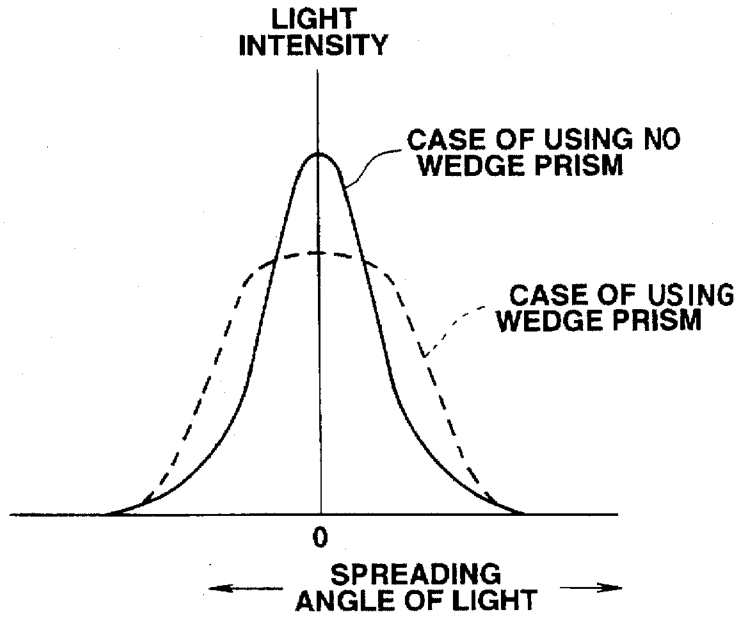
FIG. 28 is a characteristic view showing a luminous intensity of the laser line.

FIG. 28 shows the intensity distribution of the light ray which is outputted from the laser-line projection part 95 in case where the laser light-source unit 53' of the present embodiment is used. The axis of ordinate in the figure shows the luminous intensity, while the axis of abscissa indicates the spreading angle. A solid line shows case where the wedge prism 98 is not used, while a broken line shows case where the wedge prism 98 is used. It will be seen that the solid line is approximate to a Gaussian curve, but the broken line shows that the intensity is uniform. In order to improve or increase the effects of the wedge prism 98 according to the present embodiment, it is highly advantageous to use a multi-mode fiber in the optical fiber 23.

Further, the case where the intensity distribution of the laser line is uniform in this manner is advantageous, because there is no non-uniformity or unevenness in intensity in the laser line in case where a planar surface is observed substantially perpendicularly like the measurement of a turbine blade surface, for example. Conversely, the case where the wedge prism 98 is not used is advantageous in the case where the optical axis of the laser-line projection part 95 is directed toward the center direction of the pipe, that is, a portion high in intensity of the laser line is directed toward a far-point, like the case where the pipe inner surface is observed axially.

Various calculations of length measurement according to the present embodiment are similar to those in the first and second embodiments. However, the origin coordinate which corrects the third column in the table in FIG. 18 is conducted on the y-axis.

According to the present embodiment, mounting of only the electronic endoscope 82 on the measurement unit 4 enables the CPU 38 to read out the correct parameter which is set with respect to the electronic endoscope 82. Accordingly, it is possible to prevent erroneous setting of the parameter. Thus, it is possible to provide an endoscope measurement apparatus which is capable of reliably conducting the measurement.

Moreover, in the present embodiment, since the width and the color of the cursor can be modified, operation can efficiently be conducted also by a person who is anomolous trichromatism.

In connection with the above, the laser line which is projected onto the object surface is displayed by red on the observation image in view of a wavelength range of the laser light. However, the arrangement may be such that a tone of the image can be modified (color emphasis or exaggeration, exchange of a color signal which is outputted toward the side of display means, or the like, for example), so that even the person who is anomolous trichromatism can clearly identify the laser line which is displayed on the display surface, to thereby efficiently operate the measurement.

Moreover, the arrangement can also be as follows. That is, the illumination light source 3 is made to a surface-sequential illumination light source which successively outputs the illumination light of R, G and B, for example, toward the side of the object. The photographing is successively conducted by the CCD 18 under the illumination light of R, G and B of the surface sequence to thereby acquire an image of three color components. In the case of a surface-sequential image pickup system in which these color components are synthesized with each other so as to be made to a color image, timing at which the laser light is outputted toward the side of the object can be synchronized with the illumination light of the surface sequence and can be modified whereby the laser line which is displayed on the display surface is made to color which is easy to be identified from the object surface.

For example, in the case where the object surface is red, timing at which the laser light is outputted to the object surface is so set as to be synchronized with timing of the illumination light of G or B, whereby the laser light is image-picked up (recognized) as a laser line of the wavelength component of G or B, in an output image of the CCD 18. Thus, the identification of the laser line which is projected upon the object surface is made easy on an image which is image-picked up under this state.

Specifically, if the output timing of the laser light is set to the timing of the illumination light in the wavelength range which is different from the tone of the object surface in accordance with the tone, identification of the laser line on the image can easily be conducted so much regardless of the wavelength of the laser diode 56 which is actually used. In actuality, the wavelength is limited to a range in which the CCD 18 has the sensitivity.

Figure 29:
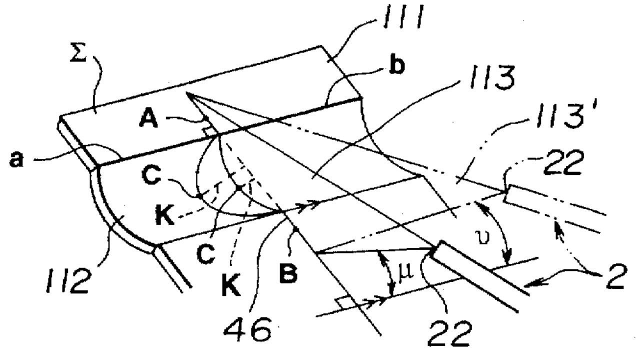
FIG. 29 is an explanatory view showing an aspect in which a depth of a groove is measured, in a fourth embodiment of the invention.

FIG. 29 shows an aspect in which a depth of a groove in a planar plate is measured by an electronic endoscope in a fourth embodiment of the present invention. The present embodiment is arranged such that, in the first embodiment, for example, judgement function is further provided for judging as to whether the laser projection surface is set perpendicularly to a face of the measurement part. This judgment function is conducted by the CPU 38 in FIG. 6.

A solid line in FIG. 29 shows a state in which a groove 112 in a planar plate 111 serving as a measurement object is observed obliquely by the electronic endoscope 2 which is used in the first embodiment, for example, and the laser line 46 is projected from the laser-line projection part 22 under an oblique observation state. In this case, the solid line shows a state in which a laser surface 113 is correctly set, while a two-dot-and-chain line shows that a laser surface 113' is not correctly set.

Specifically, in the case of the solid line, the laser surface 113 defines 90° of an angle μ with respect to a surface of the planar plate 111 in which the laser line 46 is projected. Under this state, the measurement point C on the laser line in the groove 112 is set. Thus, the length K of the perpendicular to a straight line which passes through the reference points A and B is formed, whereby it is possible to find the depth.

Meanwhile, in the case indicated by the two-dot-and-chain line, the laser surface 113 is less than 90° in angle v defined with respect to a surface of the planar plate 111 in which the laser line 46 is projected. Under this state, even if a measurement point C' on the laser line in the groove 112 is set, and a length K' of the perpendicular to a straight line which passes through the reference points A and B is found, it is impossible to find the correct depth. In view of this, in the case of such measurement object, a setting is made such that the laser line 46 is perpendicularly intersected with an edge ab of the groove 112. In this connection, a surface of the planar plate 111 is indicated by Σ.

Alternatively, a plurality of points of the length K' of the perpendicular are measured while the angle μ of the endoscope is changed. The smallest length K' is made to correct value K.

According to the fourth embodiment, it is possible to conduct the judgment as to whether or not the state is in a state in which the measurement is correctly conducted, in addition to the functional advantages of the first embodiment.

In connection with the above, in order to decide the reference straight line, it is sufficient to assign the two points A and B on the laser line of the reference surface. However, two or more points may be assigned.

Figure 30:
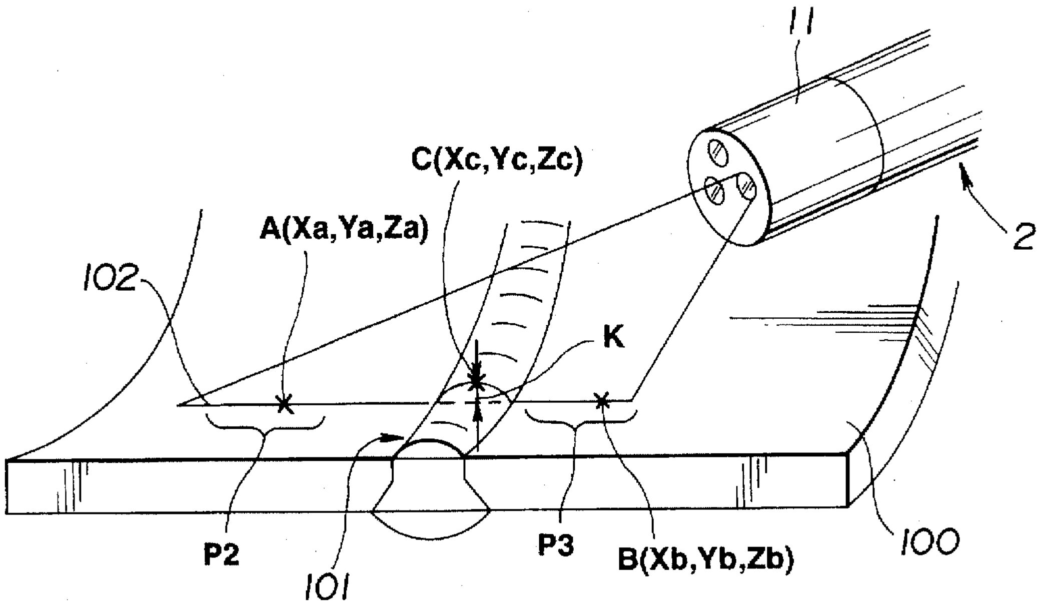
FIG. 30 is an explanatory view showing an aspect in which a projection is measured.

FIG. 30 shows an aspect in which the pipe inner surface 100 is inspected by the endoscope 2. The pipe inner surface 100 has a projection 101 due to weld penetration. FIG. 30 shows a case whereby a height of the projection 101 is measured.

Generally, whether the weld is good or poor is judged by an amount of penetration.

For this reason, the side of the distal end of the endoscope 2 is moved, the curvature part 12 is curved, or the like, to conduct the setting, such that the projection 101 is within the visual field, and a laser line 102 which is projected onto the pipe inner surface 100 passes through the projection 101.

At this time, a direction of the laser line 102 is coincident with an axial direction of the pipe to reduce the measurement error. Furthermore, the laser line 102 is projected onto the pipe inner surface 100 such that the laser line 102 passes through the measurement point C in the projection 101, which the measurement of height intends to be conducted, and extends through the reference plane which serves as the reference of the height measurement (that is, the height is zero). It is assumed that portions of the laser line 102 which are projected onto the reference surface are P2 and P3. In this case, as shown in FIG. 30, it is not necessary to set the distal-end face of the endoscope of direct vision type, in parallel with the pipe inner surface 100. The state may be a state which is observed (image picked up) obliquely.

The reference points A and B of the measurement are taken on the portions P2 and P34 of the laser line 102, by the keyboard 40, and the measurement point C in which the height is desired to be measured is indicated. The endoscope image (which is on the frame memory 36 or which is displayed on the display surface of the CRT 37) which is displayed on the display surface of the CRT 37) which is acquired under this state becomes one as shown in FIG. 31.

Figure 31:
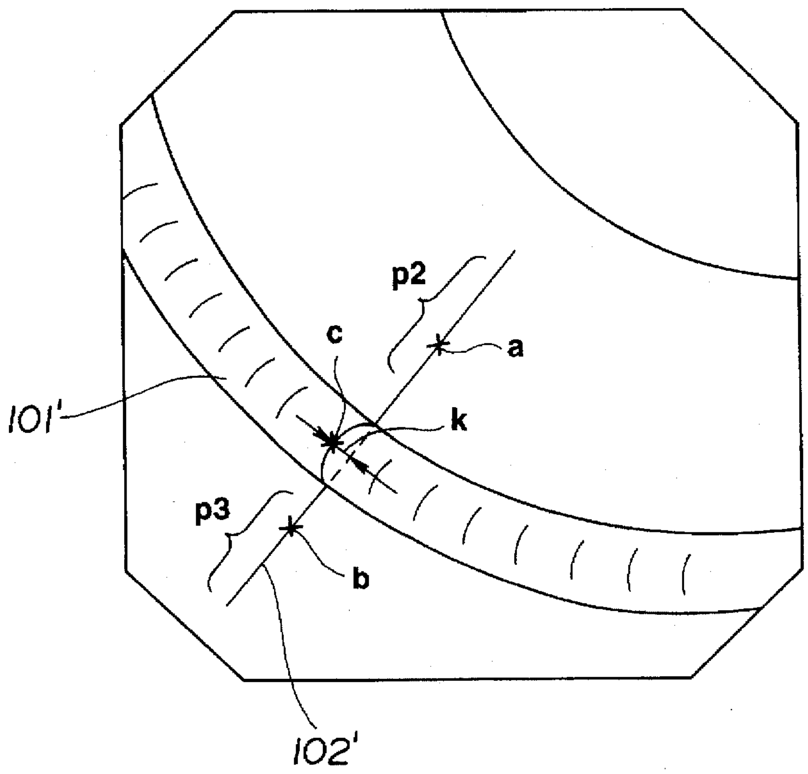
FIG. 31 is a view showing an endoscope image corresponding to that in FIG. 30.

As shown in FIG. 31, the image becomes an image in which an image 102' of the laser line is overlapped upon an image 101' of the projection, and a line direction of the laser-line image 102' is coincident with the axial direction of the pipe. Furthermore, the laser-line image 102' passes through the projection 101', and extends on the reference surface on both sides thereof. Image portions which correspond respectively to P2 and P3 in FIG. 30, that is, laser-line image portions on the reference surface become p2 and p3. Points on p2 and p3 which correspond to the actual two points A and B are a and b, and a point on the image which corresponds to the measurement point C becomes c.

The setting for the measurement has been described with reference to FIG. 30. In fact, however, the setting or the assignment is conducted on the endoscope image in FIG. 31 as follows. The CPU 38 conducts processing of the length measurement in order of the following Steps S11–S17, for example.

S11: Setting is made such that the laser-line image 102' passes on the image displayed on the CRT 37 and on the projection 101'. In this case, the distal-end side of the electronic endoscope 2 is moved, is curved or the like such that the line direction of the laser-line image 102' is made parallel to the axial direction of the pipe.

S12: The cursor is moved to a position having no irregularity on the line of the laser line image 102', and the assignment points a and b that serve as two references are assigned. The assignment points may be three or more.

S13: By the assignment of the two assignment points a and b, the CPU 38 calculates the three-dimensional coordinates of the actual reference points A and B which correspond respectively to the points a and b, on the basis of the relationship expression of the triangulation.

S14: The CPU 38 further calculates the straight line which passes through the reference points A and B, by the aforesaid expression (10').

S15: Moreover, the cursor is moved to a position of a point in which the height is intended to be measured on the line of the laser-line image 102', and the measurement assignment point c is assigned.

S16: By assignment of the measurement assignment point c, the CPU 38 calculates three-dimensional coordinate of the measurement point C corresponding to the point c, from the relational expression of the triangulation.

S17: The length K of the perpendicular which lowers from the measurement point C is found from the aforementioned expression (12), with respect to the aforesaid straight line. That is, the height (from the reference surface) of the measurement point C is calculated.

Description will be made hereunder.

Under a state set as is in FIG. 30 or FIG. 31, in order to decide the straight line which serves as the reference, three-dimensional coordinates (Xa, Ya, Za), (Xb, Yb, Zb) and (Xc, Yc, Zc) of the actual points A, B and C which correspond respectively to the two reference assignment points a and b and the measurement assignment point c can be found from the calculation or computing expression which is shown in the expressions (1)–(8).

Specifically, in the expressions (1)–(8) (and the number to which " is applied), it is assumed that the coordinates of the respective points A, B and C are the coordinate of P0 or P1. (Correspondingly thereto, it is assumed that the coordinates of the respective points a, b and c are the coordinate of the point p0 or p1), whereby it is possible to find these coordinates.

A command or the like of the coordinate computation indication is inputted from the keyboard 40 whereby the CPU 38 conducts the calculation of the coordinates of the points A, B and C by function of the measurement operation **38*a***. Depending upon the program, if the two points a and b for deciding the straight line are assigned, the points A and B may be calculated automatically. Furthermore, an expression of the straight line may also be calculated.

The straight line which passes through the A point and the B point uses the aforesaid expressions (10') and (11). Further, it is possible to find the length K of the perpendicular which lowers along the straight line of the expression (10) from the point C of the projection, by the expression (12).

In this manner, the desired height K of the projection can be found, similarly to the recess.

A fifth embodiment of the invention will subsequently be described. The present embodiment is different from the aforesaid embodiments in that a shade in the form of a line is projected onto the object surface 15, and in that a curved line, not a straight line, is used as a reference line to calculate a recess.

Figure 32:
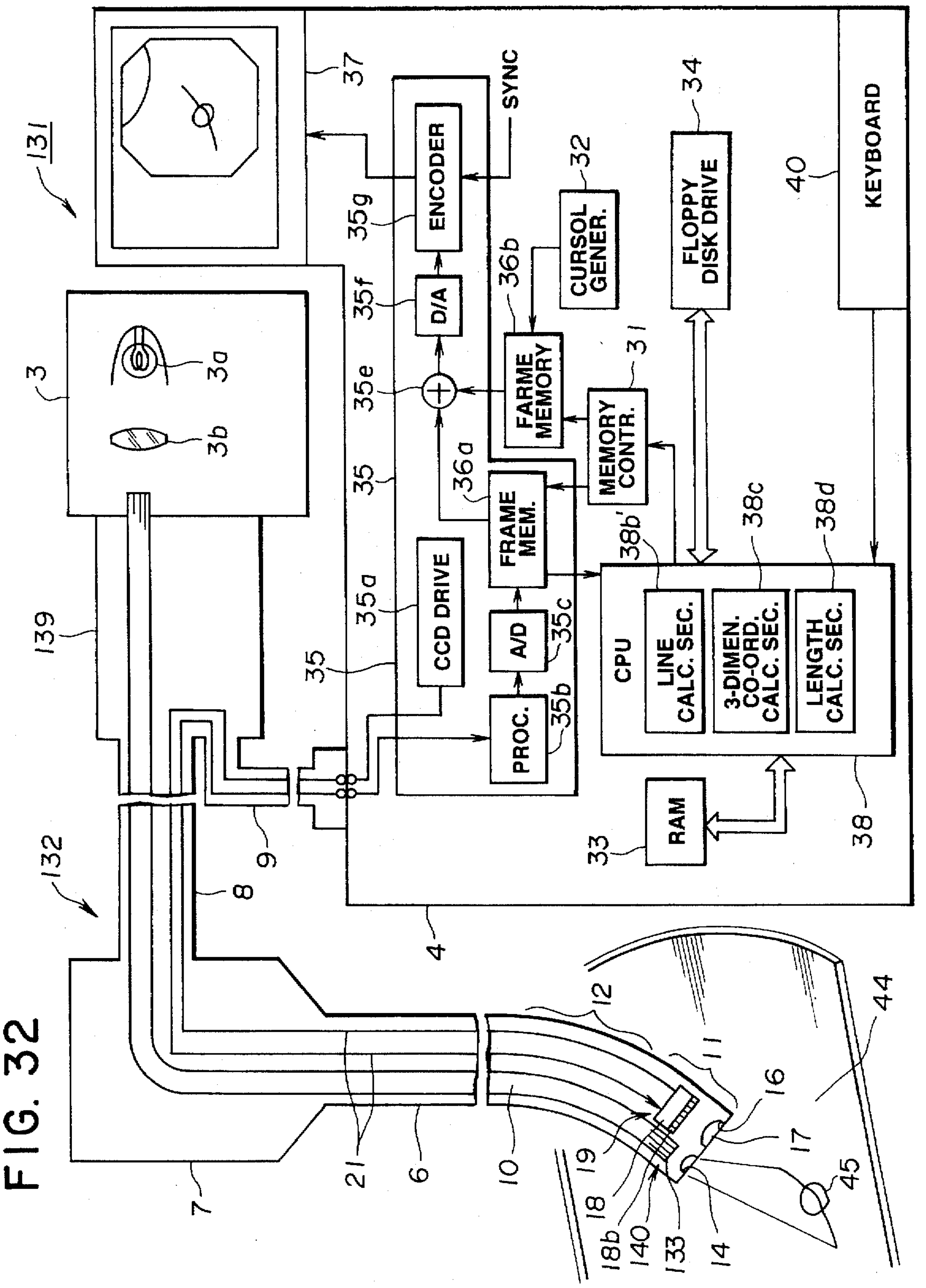

FIG. 32 shows an endoscope measurement apparatus 131 according to the fifth embodiment of the invention. An endoscope 132 which is used in the endoscope measurement apparatus 131 has, in FIG. 2, a light guide connector 144 which has no laser light-source unit 53. The light guide connector 144 is connected to the light source device 3. Further, the endoscope 132 has no optical fiber 23 for transmitting the laser light, and no laser-line projection part 22. In place thereof, as shown in detail in FIG. 33 the endoscope 132 is provided with a light blocking mask 133 for projecting a shadow in the form of a line, on the distal-end face of the light guide 10.

Figure 33:
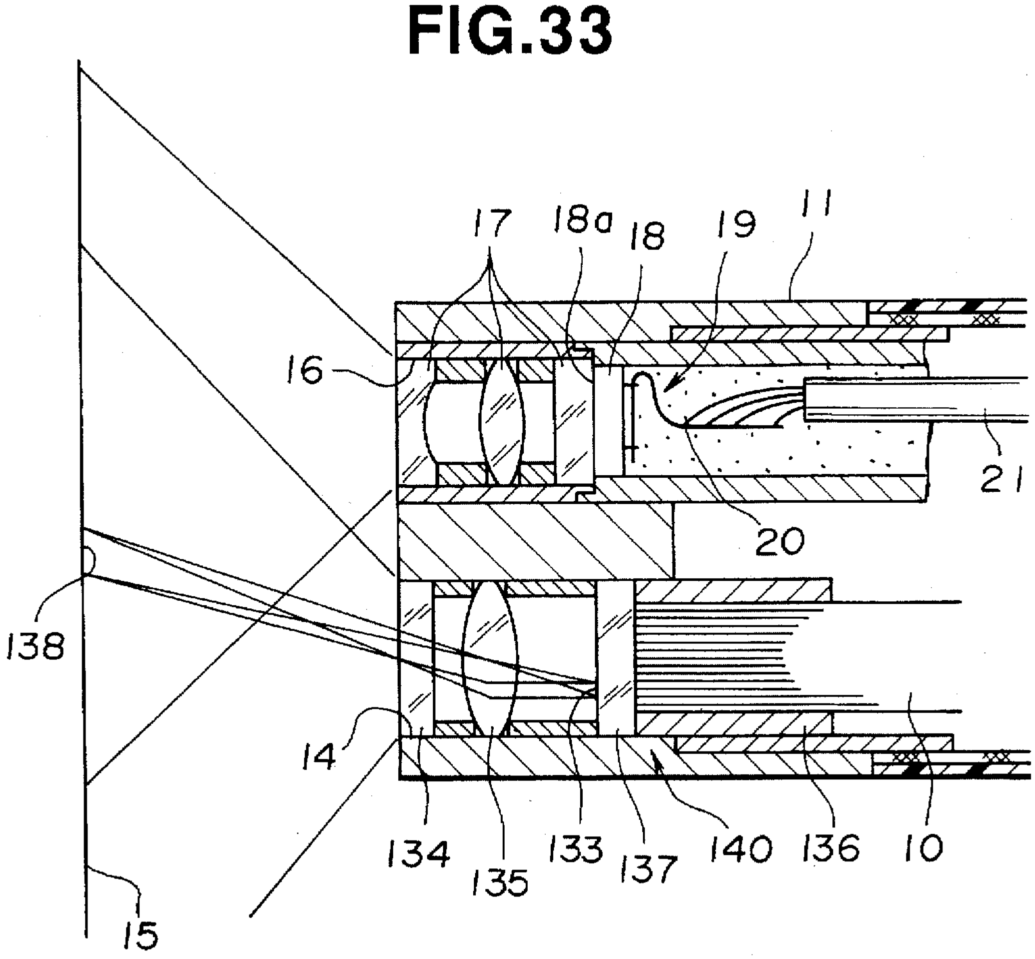

As shown in FIG. 33, the illumination window 14 (only one in this embodiment) adjacent to the observation window 16 is provided with an illumination convex lens 135 which is protected by a cover glass 134. The illumination light which is transmitted by the light guide 10 passes through the convex lens 135 and is outputted so as to spread or extract forwardly.

Figure 34:
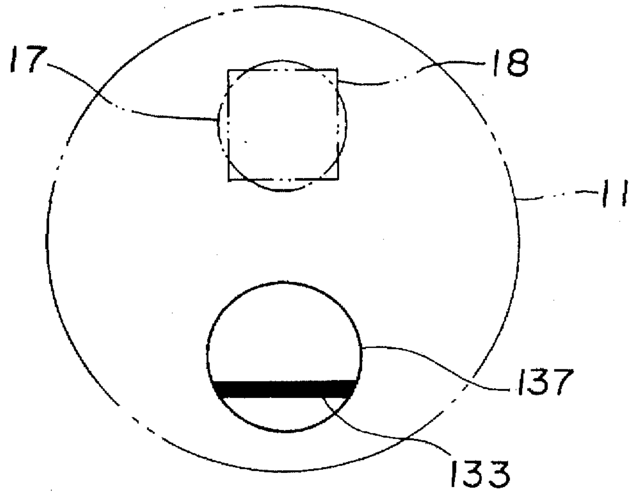

The light guide 10 has a distal-end part thereof which is fixedly mounted on the distal-end part 11 by a base 136. A glass plate 137, for example, serving as a disk-shaped plane parallel plate is mounted in front of the end face of the light guide 10. As shown in FIG. 34, the light blocking mask 133 in the form of a line is provided on a face on the side of the convex lens 135 of the glass plate 137. The light blocking mask 133 is formed such that a black paint is applied in the form of a line, or the like. A distance from the light blocking mask 133 to the convex lens 135 is substantially equal to a focal length or focal distance of the convex lens 135. The light is shielded at a portion of the light blocking mask 133, and a shadow 138 in the form of a line is projected on the side of the object surface 15. In FIG. 33, the line direction of the light blocking mask 133 is a direction which is perpendicular to the sheet of paper.

In FIG. 34, a two-dot-and-broken line indicates the object lens system 17 and the CCD 18, and shows the fact that a line direction of the light blocking mask 133 is parallel to a longitudinal direction or a lateral or transverse direction of a square or rectangular image pickup surface of the CCD 18.

Moreover, a measurement unit 4' in the present embodiment has a structure in which the laser-diode drive circuit 39 is deleted from the measurement unit 4 in FIG. 2, and the measurement unit 4' has a curvature calculation part **38*b*' in place of the line calculation part 38*b* in the CPU 38. The other arrangement of the hardware is similar to that of FIG. 2. The same numerals are applied to constitutional elements the same as those in FIG. 2**, and the description thereof will be omitted.

Image projection means 140 which forms the shade in the form of a line, in the present embodiment, is realized by the fact that the light shielding mask 133 is provided on an illumination optical system portion. Accordingly, the arrangement of the endoscope measurement apparatus 131 is more simplified than that in the first embodiment.

Figure 35A:
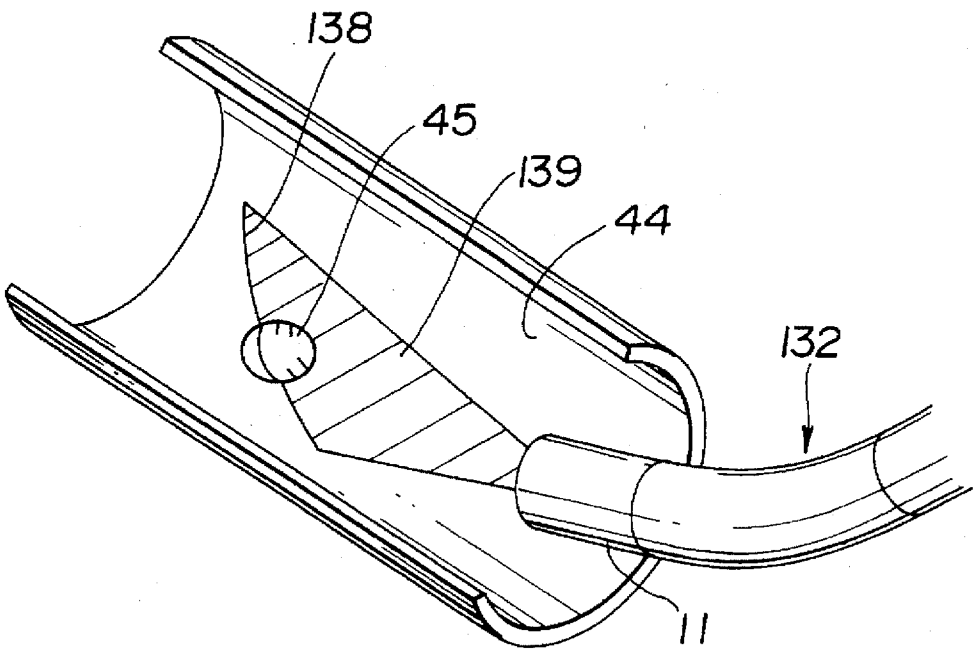
FIG. 35A is an explanatory view showing an aspect in which a shadow in the form of a line is projected onto a pipe inner surface having a recess.
Figure 36:
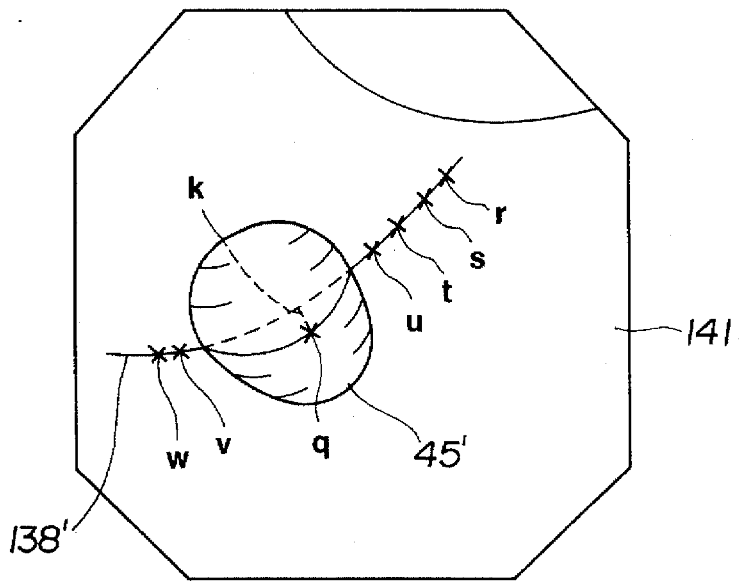

FIG. 35A shows an aspect in which the recess 45 such as the wall reduced part or the like of the cylindrical pipe inner surface 44 is measured. In the case where the shadow 138 which is projected onto the pipe inner surface 44 is inclined with respect to the axis of the pipe, an image 141 as shown in FIG. 36 is displayed on the CRT 37. As will be seen from the image 141, a shadow 138' becomes a curved line. In the present embodiment, the following is carried out to find three-dimensional expression of the curved line which is projected onto the pipe inner surface 44, to measure the depth of the recess 45.

Six points including r, s, t, u, v and w, for example, are assigned, by the cursor, to optional positions on the curved line, except for the recess, in the image 141. Subsequently, q is assigned on the curved line which passes through the recess, as measurement points of the depth.

Figure 35B:
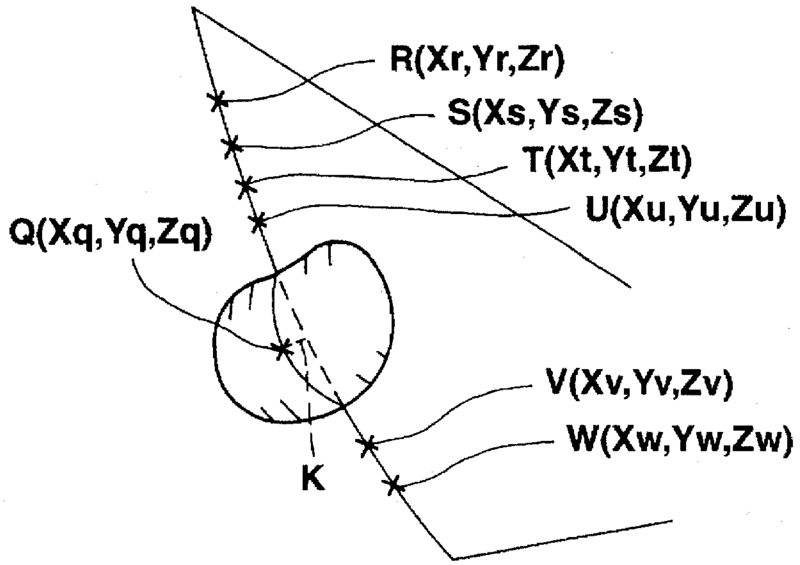
FIG. 35B is a view in which a part of FIG. 35A is enlarged.

By the assignment of these points, the CPU 38 calculates the three-dimensional coordinates of the points which correspond respectively to the points assigned in the image, by the use of the expressions (1)–(8). The three-dimensional coordinates in which points R, S, T, U, V, W and Q which correspond to the point r, s, t, u, v, w and q are calculated are shown in FIG. 35B.

Figure 37:
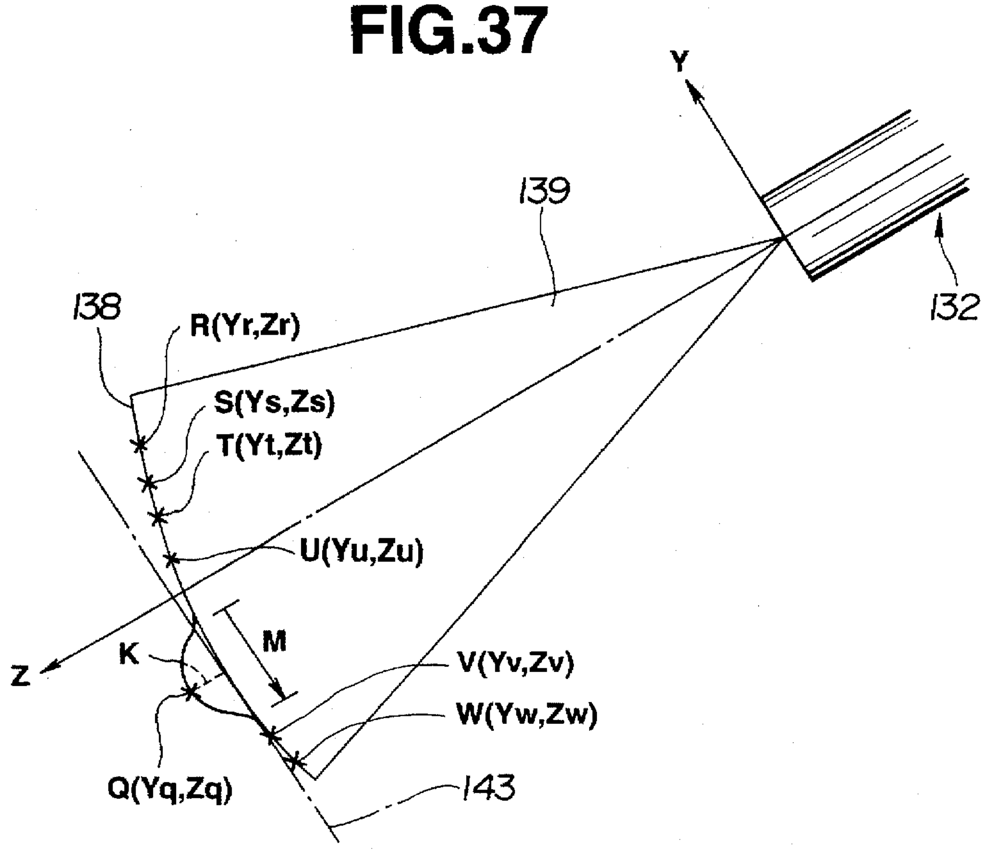

In the case where an expression of an approximate curved line which expresses a curved line passing through the six points including the points R, S, T, U, V, W and Q which are expressed by the three-dimensional coordinate, on the pipe inner surface 44 is found, it is considered in a coordinate system that a planar surface of a projection planar surface 139 which is cut by the shadow 138 so projected as to pass through the recess 45 in the pipe inner surface 44 upon which the shadow 138 is projected is made to a YZ coordinate system, for example, as shown in FIG. 37, for example. Specifically, coordinate conversion should be made to the projection planar surface 139.

In this manner, consideration is made to the projection planar surface 139 which includes the shadow 138, whereby a curved-line portion projected upon the pipe inner surface except for the recess in the projected shadow 138 can be approximated by a curved line within the planar surface, as follows. As shown in FIG. 12A and FIG. 12B, optional points P0 and P1 on the projected line exist at a position on the line which is parallel to a Y-axis (that is, X=–H) where an X coordinate is spaced H from the Y-axis and, accordingly, if the coordinate conversion in which a value of the X-coordinate is subtracted also by –H (that is, a three-dimensional coordinate (X–H, Y, Z) is made to a new three-dimensional coordinate (X,Y,Z)) is conducted, the projected planar surface 139 resides on a YZ planar surface of X=0. Thus, it is made possible to conduct consideration by a coordinate system which the YZ coordinate system. Since the value of X is constant, a YZ coordinate system of a YZ planar surface in which X=H may be adopted.

More specifically, the curved line except for the recess 45 in the shadow 138 which is so projected as to pass through the recess 45, upon the pipe inner surface, is approximated by a secondary expression, and is made to the reference curved line of the depth measurement. A general expression of the secondary curved line is indicated as follows:

$$aY^2+2hYZ+bZ^2+2gY+zfZ+c=0 \tag{21}$$

Here, a, h, g, b, f and c are constants.

The coordinate (Y, Z) of the above-described R, S, T, U, V, and W is substituted into the expression (21) to make these six expressions simultaneous with each other so that it is possible to find the six constants a, h, g, b, f and c. Specifically, since the six constants a, h, g, b, f and c are decided, an expression of the curved line which serves as the reference can be found specifically.

The depth of the recess 45 is subsequently found. A tangent line of an optional point (Y1, Z1) can be expressed by a secondary expression which is expressed by the expression (21), by the following expression:

$$Y(aY1+hZ1+g)+Z(hY1+bZ1+f)=(gY1+fZ1+c)=0 \tag{22}$$

Here, if A'=aY1+hZ1+g,

B'=hY1+bZ1+f, and

C'=gY1+fZ1+c, the following expression can be acquired:

$$A'Y+B'Z+C'=0 \tag{23}$$

A length D of the perpendicular which lowers to a tangent line 143 which is expressed by the expression (23) from a point Q (Yq, Zq) which finds the depth of the recess 45 is expressed by the following expression:

$$D=|A'Yq+B'Zq+C'|/(A'^2+B'^2)^{1/2} \tag{24}$$

Here, in the case where the point Q which finds the depth exists on the convex side of the curved line which is expressed by the expression (21), the afore-mentioned optional point (Y1, Z1) is varied within the range of M 142 in FIG. 37, and a value at which the length D of the perpendicular is the maximum at the respective points is assumed to be the depth K.

Further, in the case where the point Q which is directed to find the depth exists on the concave side of the curved line which is expressed by the expression (21), the aforesaid optional point (Y1, Z1) is varied within the range of M in FIG. 37, and the length D of the perpendicular is found at the respective points. A value at which D is the smallest is assumed to be the depth K.

In the present embodiment, the secondary expression has been used as the reference line. However, the other mathematical functions may be used. Moreover, it will be clear that the height of the projection due to the wall-reduced part, not the depth of the recess 45 due to the same, is also similarly found.

Furthermore, in the present embodiment, the illumination light for observation is utilized to form the means for projecting the shadow. Accordingly, the laser light source is unnecessary, or is not required. The system can be formed by utilization of a large portion of the existing endoscope apparatus, or by a slight reconstruction or reorganization thereof. Accordingly, the endoscope measurement system can be realized which can measure also the depth of the recess or the height of the projection at low cost.

The above-described embodiment has been arranged as follows. That is, an optional point is assigned within the observation image of the light in the form of a line or within the shadow in the form of a line on the projected object surface. The approximate expression of the three-dimensional reference line which passes through the assigned point is found. Subsequently, the measurement point such as the recess or the like is assigned. The length of the perpendicular which lowers from the three-dimensional coordinate position of the measurement point, to the reference line, or the like, is found to find the depth of the recess or the like.

To the contrary, the arrangement may be as follows, like a sixth embodiment to be described later. Specifically, a point which serves as the reference on a projected line is utilized to find three-dimensional expression of a reference line. A measurement point which is desired to conduct measurement is assigned. A length of a perpendicular which lowers from a three-dimensional coordinate position of the measurement point to a reference line, or the like is found, to find the depth of the recess, or the like.

In connection with the above, in the above-described various embodiments, the endoscope which is used for length measurement should not be limited to the electronic endoscope, but may be a TV-camera mounting scope in which an optical image due to an object lens is formed by a fiber bundle or the like, a solid-state image pickup element is built in an ocular part or the like of an optical endoscope (optical scope) which is provided with function of an image guide which transmits the optical image, and the scope is mounted on a TV camera.

Further, a display device for displaying an image should not be limited to the CRT 37, but may be one which uses a liquid crystal display, a plasma display, or the like. Moreover, the arrangements in which the above-described embodiments are combined with each other partially or the like to form different embodiments belong to the present invention.

What is claimed is:

1. An endoscope measurement apparatus comprising:

an endoscope having an elongated insertion part, an illumination optical system provided on the distal end of said insertion part, for outputting an illumination light to an object, an object optical system provided on the distal end of said insertion part for focusing an image of the object which is illuminated by said illumination light, reference-line projection means provided on the distal end of said insertion part for projecting a single reference line which passes through a recess or a projection residing on a plane of said object, and an image pickup element for photoelectrically converting an image on the basis of said object optical system;

signal processing means which conducts signal processing with respect to said image pickup element, to generate an image signal;

display means into which said image signal is inputted, for displaying an image corresponding to said object upon which said reference line is superimposed;

position assignment means for assigning a position of said image; and operation means for carrying out calculation of an expression of an approximate line which three-dimensionally approximates the reference line passing through said plane, the operation means calculating a three-dimensional coordinate position corresponding to a point which is assigned by said position assignment means, on the reference line which passes through said recess or said projection, and the operation means calculating the depth of said recess or the height of the projection by an operation using a distance between said approximate line and said three-dimensional coordinate position.

2. An endoscope measurement apparatus according to claim 1, wherein, whenever the plane of said object is a cylindrical surface, the reference line which passes through said plane is set in a direction which is in parallel with an axis of said cylindrical surface.

3. An endoscope measurement apparatus according to claim 1, further comprising correction means for correcting at least one of an error and distortion of the object optical system of said endoscope when the three-dimensional coordinate of a position which is assigned by said position assignment means is determined.

4. An endoscope measurement apparatus according to claim 1, wherein said reference-line projection means outputs a light in the form of a line from a laser light which is supplied from a semiconductor laser, to form said reference line on said object.

5. An endoscope measurement apparatus according to claim 1, wherein said reference-line projection means projects a shadow in the form of a line, onto said object, to form said reference line by said shadow in the form of a line.

6. An endoscope measurement apparatus according to claim 1, wherein said reference-line projection means projects a shadow in the form of a line due to a light shielding part in the form of a line which is provided on said illumination optical system, onto said object, to form said reference line by said shadow in the form of a line.

7. An endoscope measurement apparatus according to claim 4, wherein said endoscope includes transmission means for transmitting the illumination light to said illumination optical system, and wherein said transmission means includes a connector part which is connected to an illumination light-source device for generating an illumination light, which is provided on the outside of said endoscope, and has a laser light source having said semiconductor laser on said connector part.

8. An endoscope measurement apparatus according to claim 4, comprising an optical fiber for transmitting said laser light to said reference-line projection means, wherein a wedge-shaped prism is provided on an end face of said optical fiber to which said laser light is supplied.

9. An endoscope measurement apparatus according to claim 1, wherein a line direction of said reference line which is projected from said reference-line projection means toward the side of said object is in parallel with a longitudinal direction of a rectangular image pickup surface of said image pickup element.

10. An endoscope measurement apparatus according to claim 3, comprising a plurality of said endoscopes, wherein said correction means has recording means for recording information for correcting at least one of the error and the distortion of the respective object optical systems of said plurality of endoscopes, and wherein said correction means reads out information corresponding to an endoscope which was last-used, to carry out correction.

11. An endoscope measurement apparatus according to claim 10, comprising a semiconductor memory which records thereon information which is to be corrected by said correction means for every one of said endoscopes, wherein said correction means reads out said information from the last-used endoscope, to carry out the correction.

12. An endoscope measurement apparatus according to claim 1, wherein said operation means comprises a CPU.

13. An endoscope measurement apparatus according to claim 1, wherein said endoscope is a direct vision endoscope in which a direction in parallel with a longitudinal axis of said insertion part is an observation visual field.

14. An endoscope measurement apparatus according to claim 1, wherein said endoscope is a side looking endoscope in which a direction perpendicular to a longitudinal axis of said insertion part is an observation visual field.

15. An endoscope measurement apparatus according to claim 1, wherein said position assignment means is cursor display means for positioning a cursor at an optional position within said image.

16. An endoscope measurement apparatus according to claim 1, wherein said operation means calculates three-dimensional coordinate positions which correspond respectively to a plurality of points which are assigned on the reference line passing through said plane, to find an expression of said approximate line from operation to calculate an expression of the line which passes through said three-dimensional coordinate positions.

17. A method of measuring a depth of a recess or a height of a projection, comprising:

a first step of projecting a light or a shadow in the form of a single line from a reference-line projection means which is provided on the side of a distal end of an endoscope which is provided with image pickup means, onto a plane of an object in or on which the recess or the projection resides, to form a reference line which passes through said plane, and said recess or said projection;

a second step of image-picking up said object by said image pickup means, to assign a plurality of points on the reference line which passes through said plane in the image of said object which is displayed by said display means;

a third step of assigning a measurement point to measure the depth or the height of said recess or projection at said measurement point along the reference line which passes through said recess or said projection in an image of said object; and a fourth step of conducting calculation of the expression of the approximate line which expresses three-dimensionally the reference line which passes through said plane and which serves as the reference of measurement and calculation of a three-dimensional coordinate of said measurement point, by the assignment of said plurality of points, and further calculating a distance from said measurement point to said approximate line to calculate the depth of said recess or the height of said projection.

18. A measurement method according to claim 17, wherein said reference line which passes through said plane and the recess or the projection is projected so as to substantially perpendicularly cut said plane and the recess or the projection.

19. A measurement method according to claim 17, wherein said approximate line is a straight line.

20. A measurement method according to claim 17, wherein the assignment of said measurements point and said plurality of points is designated by a cursor which is moved within said image.

21. A measurement method according to claim 17, wherein the calculation of the expression of said approximate line, the calculation of said three-dimensional coordinate, and the calculation of said depth or said height are carried out by a CPU.

22. A measurement method according to claim 17, wherein said light in the form of a reference line is light having a wavelength of 600–700 nanometers.

23. A measurement method according to claim 20, wherein at least one of a width of said cursor and a display color of said cursor is selectable.

24. A measurement method according to claim 19, wherein the assignment of said plurality of points is two points or three points.

25. A measurement method according to claim 19, wherein said calculation of the distance is arranged such that a length of a perpendicular which extends from said measurement point to said approximate line is calculated, and said length of the perpendicular is the depth of said recess or the height of said projection.

26. A measurement method according to claim 17, wherein said approximate line is a curved line.

27. A measurement method according to claim 26, wherein said calculation of the distance is arranged such that a length of a perpendicular which extends to a tangent of said curved line from said measurement point is calculated, and said length of the perpendicular is the depth of said recess or the height of said projection.

28. A measurement method according to claim 17, wherein the assignment of said plurality of points includes six points.

29. An endoscope measurement apparatus according to claim 1, wherein a line direction of said reference line which is projected from said reference-line projection means toward the side of said object is in parallel with a lateral direction of a rectangular image pickup surface of said image pickup element.

* * * * *